United States Patent
Kim et al.

(10) Patent No.: US 7,105,133 B2
(45) Date of Patent: Sep. 12, 2006

(54) FLUID SAMPLING APPARATUS AND FLUID ANALYZER HAVING THE SAME

(75) Inventors: Dong-Hyun Kim, Yongin-si (KR); Do-Hyun Cho, Yongin-si (KR); Woo-Dong Sung, Suwon-si (KR); Jin-Suk Kim, Yongin-si (KR); Won-Suk Choi, Yongin-si (KR)

(73) Assignee: Samsung Electronics, Co., Ltd. (KR)

( * ) Notice: Subject to any disclaimer, the term of this patent is extended or adjusted under 35 U.S.C. 154(b) by 638 days.

(21) Appl. No.: 10/253,023

(22) Filed: Sep. 24, 2002

(65) Prior Publication Data

US 2003/0064007 A1  Apr. 3, 2003

(30) Foreign Application Priority Data

Sep. 28, 2001  (KR) .................................. 01-60576

(51) Int. Cl.
- *B01L 3/02* (2006.01)
- *B01L 11/00* (2006.01)
- *G01N 21/00* (2006.01)
- *G01N 15/00* (2006.01)

(52) U.S. Cl. .......................... 422/100; 422/63; 422/64; 422/67.1; 422/103

(58) Field of Classification Search ................. 422/65, 422/100, 63, 67, 68.1, 93, 103, 64
See application file for complete search history.

(56) References Cited

U.S. PATENT DOCUMENTS

| | | | |
|---|---|---|---|
| 3,915,652 A * | 10/1975 | Natelson .................... 422/65 |
| 4,108,602 A * | 8/1978 | Hanson et al. ............... 436/52 |
| 5,167,926 A * | 12/1992 | Kimura et al. ............... 422/67 |
| 5,196,169 A * | 3/1993 | Schick et al. ................ 422/81 |
| 5,416,023 A * | 5/1995 | Binder et al. ............. 435/287.9 |
| 5,681,531 A * | 10/1997 | LaPack et al. ............... 422/81 |
| 5,841,022 A | 11/1998 | Hase ........................ 73/23.22 |
| 5,908,599 A * | 6/1999 | Behringer et al. ............ 422/50 |
| 6,170,494 B1 * | 1/2001 | Marinaro et al. ......... 134/22.18 |
| 6,350,617 B1 * | 2/2002 | Hindsgaul et al. .......... 436/173 |
| 6,423,536 B1 * | 7/2002 | Jovanovich et al. ...... 435/287.2 |
| 6,599,477 B1 * | 7/2003 | Miyake et al. ............... 422/64 |
| 6,706,527 B1 * | 3/2004 | Szecsody .................... 436/25 |
| 6,787,111 B1 * | 9/2004 | Roach et al. ................. 422/99 |

(Continued)

FOREIGN PATENT DOCUMENTS

JP  6-094733  8/1994

(Continued)

*Primary Examiner*—Brian R. Gordon
(74) *Attorney, Agent, or Firm*—Mills & Onello LLP

(57) ABSTRACT

A fluid sampling apparatus and associated fluid analyzer sample process fluids used in semiconductor manufacturing at a plurality of measurement points. The fluid sampling apparatus includes a first nozzle assembly having a plurality of outlet nozzles. The plurality of outlet nozzles are connected to lines supplying the process fluids. A second nozzle assembly is installed above the first nozzle assembly and includes an inlet nozzle connected to an apparatus for measuring a contamination level of the process fluids. A motor is connected to the second nozzle assembly to align a selected outlet nozzle with the inlet nozzle. A pneumatic cylinder is coupled to the first nozzle assembly to connect the selected outlet nozzle with the inlet nozzle. In this manner, it is possible to measure the contamination level of process fluids supplied at a plurality of measurement points by using a single measuring apparatus.

24 Claims, 12 Drawing Sheets

U.S. PATENT DOCUMENTS

| | | |
|---|---|---|
| 6,887,429 B1 * | 5/2005 | Marshall et al. ............... 422/81 |
| 6,902,938 B1 * | 6/2005 | Cody ......................... 436/174 |
| 2001/0005489 A1 * | 6/2001 | Roach et al. ................. 422/99 |
| 2002/0106804 A1 * | 8/2002 | Tanaka ....................... 436/54 |
| 2002/0131896 A1 * | 9/2002 | Hunnell et al. ............... 422/67 |
| 2002/0164821 A1 * | 11/2002 | Brink et al. ................. 436/180 |
| 2003/0053937 A1 * | 3/2003 | Akporiaye et al. ........... 422/99 |
| 2003/0072679 A1 * | 4/2003 | Johnson et al. ............... 422/63 |

FOREIGN PATENT DOCUMENTS

| | | |
|---|---|---|
| JP | 7-209239 | 8/1995 |
| JP | 9-196828 | 7/1997 |
| JP | 9-318609 | 12/1997 |

* cited by examiner

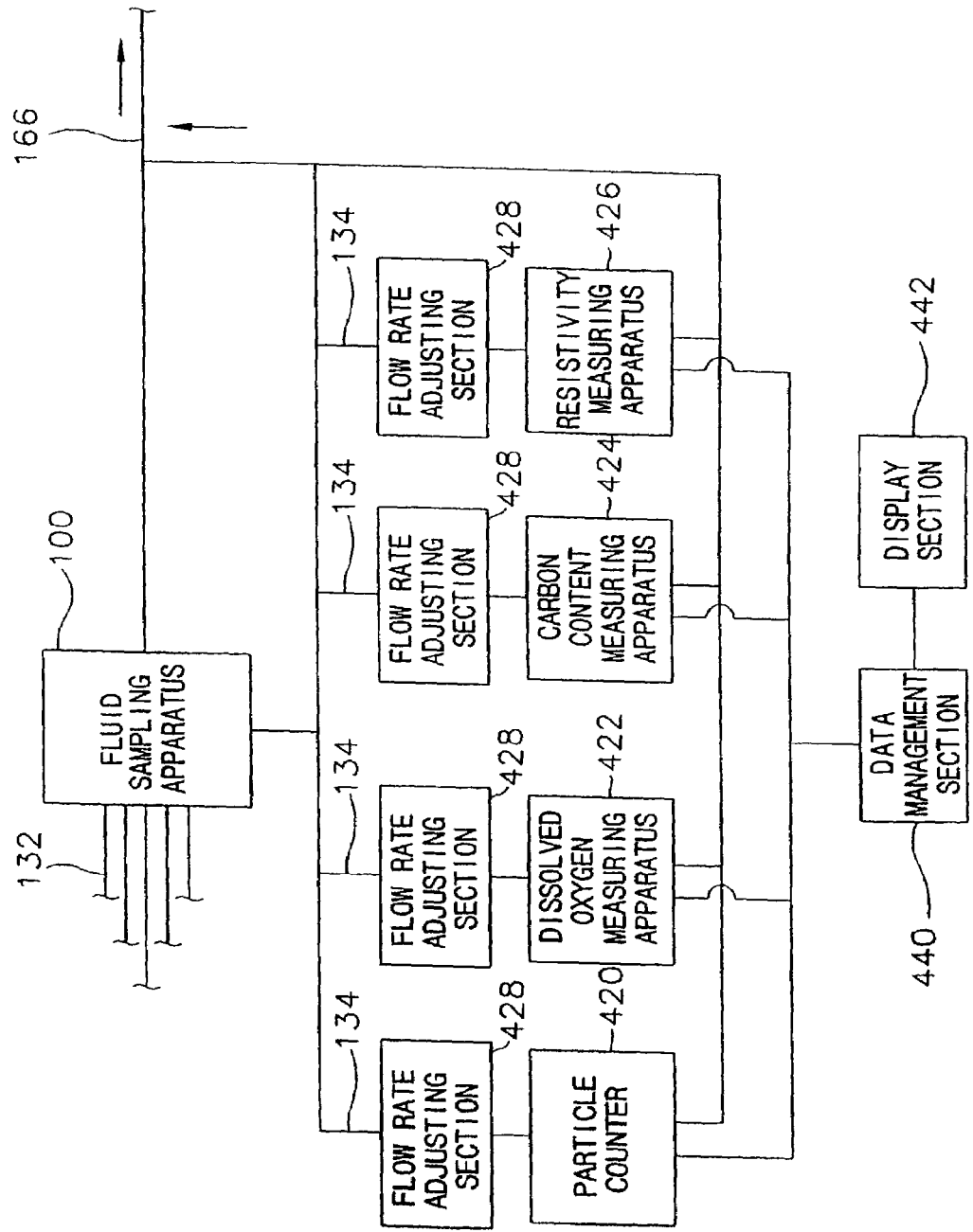

FLUID SAMPLING APPARATUS AND FLUID ANALYZER HAVING THE SAME

BACKGROUND OF THE INVENTION

1. Field of the Invention

The present invention relates to a fluid analyzer used in a semiconductor manufacturing process, and more particularly to a fluid analyzer capable of sampling process fluids used in a semiconductor manufacturing process for analyzing the process fluids.

2. Description of the Related Art

Generally, semiconductor devices are manufactured by performing a series of unit processes for forming a film, a pattern, and a metal wiring structure on a semiconductor substrate. While the individual unit processes are carried out, more than 40 kinds of gases with responsive, corrosive, and noxious properties and various process fluids including deionized water are used. Such gases can be directly used in a semiconductor manufacturing process as process gases, or can be used as auxiliary gases for maintaining a process environment. In addition, they can be used as carrier gases for moving the process gases to a process chamber in which a process is carried out. Deionized water is used for cleaning the semiconductor substrate between unit processes.

In view of this, the cleanliness of such gases or deionized water directly influences the yield and productivity of the semiconductor devices. That is, if such gases or deionized water contain too many impurities exceeding a predetermined reference level permitted in the unit processes, process failures can occur. Accordingly, the density of impurities and the number of particles in such gases or deionized water are periodically measured through an analyzing process using a fluid analyzer.

Lines for supplying process fluids into devices carrying out the unit processes are widely divided into a main line and a plurality of sub-lines, which branch from the main line and connect to the devices carrying out the unit processes. Process fluids can also be contaminated while passing through each line. Contamination levels in the main line and sub-lines are often times different from each other.

Therefore, in order to improve the productivity of the semiconductor devices, it is preferable to analyze the process fluids by sampling the process fluids from the sub-lines supplying the process fluids. However, it is an expensive undertaking to install the fluid analyzers on the sub-lines. For this reason, the analyzing process is carried out only with respect to the process fluid sampled at the main line. Accordingly, when a process failure occurs in the form of a contamination of the process fluids, much time is required to find a contamination source, thereby lowering the productivity of the semiconductor devices. In order to solve the above problem, studies for analyzing process fluids sampled from a plurality of lines with using a common fluid analyzer have been actively developed.

For example, Japanese Laid-Open Patent Publication No. 6-094733 to Shimada, et al. discloses a switching method for measuring impurities in a plurality of pipes using one fluid analyzer. According to the Shimada's disclosure, a plurality of gas pipes are respectively installed on the fluid analyzer and impurities contained in gases of the plural gas pipes are measured by switching the fluid analyzer with respect to the plurality of gas pipes. Japanese Laid-Open Patent Publication Nos. 9-318609 to Inomata, et al. and 9-196828 to Inomata disclose a gas analyzer having a gas switching device and a gas adjusting section for allowing plural gases to be selectively supplied into the gas analyzer. U.S. Pat. No. 5,841,022 to Hase discloses a gas analyzer and a gas analysis method. According to the Hase disclosure, the contamination of a clean environment is controlled by collecting samples from a plurality of measurement points while switching between these points.

SUMMARY OF THE INVENTION

The present invention addresses the limitations of the conventional approaches. It is therefore an object of the present invention to provide a fluid analyzer including a fluid sampling apparatus, in which an apparatus for measuring a contamination of process fluids is selectively connected to a plurality of lines supplying the process fluids used in a semiconductor manufacturing process.

To achieve the object of the present invention, according to a first aspect of the present invention, there is provided a fluid sampling apparatus comprising a first nozzle assembly including a plurality of outlet nozzles connected to fluid lines for supplying a fluid from the fluid lines, a second nozzle assembly installed in opposition to the first nozzle assembly and including an inlet nozzle for receiving the fluid from a nozzle selected from the outlet nozzles, and a driving system for selecting a nozzle from the outlet nozzles and for connecting and separating the selected outlet nozzle to and from the inlet nozzle.

The first nozzle assembly further includes a first plate having a disc shape. A plurality of first fluid passages are formed along a periphery of the first plate, while passing through the first plate, and the outlet nozzles are connected to first sides of the first fluid passages, respectively. In addition, the second nozzle assembly further includes a second plate having a disc shape, and the inlet nozzle is connected to a first side of the second plate.

The driving system includes a rotating shaft connected to a central portion of the second plate, a motor connected to the rotating shaft for matching a central axis of the nozzle selected from the outlet nozzles with a central axis of the inlet nozzle, and a pneumatic cylinder connected to the first plate for connecting and separating the inlet nozzle to and from the outlet nozzle.

The second fluid passage connected to the inlet nozzle passes through a center axis of the rotating shaft, and the second fluid passage extends from a central portion of the second plate to the inlet nozzle by passing through the second plate.

The second nozzle assembly further includes a plurality of auxiliary inlet nozzles connected to the first side of the second plate corresponding to outlet nozzles except for the outlet nozzle selected by the motor, a plurality of third fluid passages are formed along a periphery of the second plate while passing through the second plate, and the auxiliary inlet nozzles are connected to the third fluid passages, respectively. A sectional area of the third fluid passage is formed smaller than a sectional area of the second fluid passage so as to reduce the loss of the fluid through the auxiliary inlet nozzles connected to the non-selected outlet nozzles.

In one embodiment, the outlet nozzle and the inlet nozzle are comprised of Teflon, and the first and second plates are comprised of Teflon or stainless steel. First ends of the outlet nozzles are formed in a convex conical shape, and a first end of the inlet nozzle connected to the nozzle selected from outlet nozzles is formed in a concave conical shape.

The fluid sampling apparatus may further include control unit, which is connected to the driving system and controls an operation of the driving system so as to align the selected outlet nozzle with the inlet nozzle and to reciprocate the second nozzle assembly for connecting and separating the selected outlet nozzle to and from the inlet nozzle.

When the fluid includes deionized water, the fluid sampling apparatus may further have a container receiving the first and second nozzle assemblies therein and containing deionized water continuously supplied from the outlet nozzles, a drain line connected to a side portion of the container for draining deionized water from the container, a water level detecting sensor installed in the container for detecting a level of deionized water, and a valve installed in the drain line for adjusting a draining amount of deionized water based on a signal from the water level detecting sensor. The first and second nozzle assemblies are preferably immersed in deionized water contained by the container.

In addition, the fluid sampling apparatus further comprises a plurality of first sampling lines connected to the outlet nozzles, a plurality of second sampling lines connected to the fluid lines, and a plurality of connectors installed at another side of the container for connecting the first sampling lines with the second sampling lines.

When the fluid is any one selected from the group consisting of air, nitrogen, oxygen, and argon, the fluid sampling apparatus further comprises an enclosed container having the first and second nozzle assemblies therein, a drain line connected to the enclosed container for draining the fluid continuously supplied from the outlet nozzles into the enclosed container, a pressure sensor installed in the enclosed container for sensing an internal pressure in the enclosed container, and a valve installed in the drain line for adjusting a draining amount of the fluid based on a signal from the pressure sensor. Alternatively, the pressure sensor and the valve can be replaced with a pressure control valve installed in the drain line.

When an inner diameter of the outlet nozzle is about ¼ inch and the pressure of the process fluid to be supplied is about 3 to 6 kg/cm$^2$, a distance between the outlet nozzle and the inlet nozzle is preferably about 5 to 10 mm.

According to another embodiment of the present invention, the driving device includes a pneumatic cylinder connected to the first nozzle assembly for reciprocating the first nozzle assembly, and a two-axis Cartesian coordinate robot connected to the second nozzle assembly for driving the second nozzle assembly such that selected outlet nozzle is aligned with the inlet nozzle.

According to still another embodiment of the present invention, the driving device includes a three-axis Cartesian coordinate robot connected to the second nozzle assembly for aligning the selected outlet nozzle with the inlet nozzle and for connecting and separating the selected outlet nozzle to and from the inlet nozzle.

In this manner, the first and second nozzle assemblies driven by the driving system can selectively sample the fluid from the fluid lines.

To achieve the object of the present invention, according to a second aspect of the present invention, there is provided a fluid analyzer comprising a fluid sampling unit including a first nozzle assembly having a plurality of outlet nozzles connected to fluid lines for supplying a fluid from the fluid lines, a second nozzle assembly installed in opposition to the first nozzle assembly and having an inlet nozzle for receiving the fluid from a selected one of the outlet nozzles, and a driving system for selecting the selected outlet nozzle and for connecting and separating the selected outlet nozzle to and from the inlet nozzle, a measuring unit connected to the inlet nozzle for measuring a contamination level of the fluid supplied through the selected outlet nozzle and the inlet nozzle, and a data management unit connected to the measuring device so as to store and manage data measured by the measuring device.

When the fluid includes deionized water, the measuring unit includes a particle counter for measuring a number of particles contained in the fluid, a dissolved oxygen measuring apparatus, a carbon content measuring apparatus, and a resistivity measuring apparatus.

When the fluid is any one selected from the group consisting of air, nitrogen, oxygen, and argon, the measuring unit includes a particle counter for measuring a number of particles contained in the fluid.

The fluid analyzer further comprises a third sampling line for connecting the inlet nozzle to the measuring unit and a flow rate adjusting section, which is installed in the third sampling line so as to adjust a flow rate of the fluid supplied into the measuring unit.

The fluid analyzer further comprises display unit connected to the data management unit for displaying the data measured by the measuring unit in real time and for displaying the data stored in the data management section.

Accordingly, the contamination level of the fluid sampled from a plurality of fluid lines can be measured using a single measuring unit and the data management unit. In addition, it is possible to compare and analyze the measured data. By storing and managing the compared and analyzed data, the cost required for installing additional fluid analyzers can be eliminated and the cleanliness of the fluid can be effectively inspected.

In addition, by applying the fluid sampling apparatus and the fluid analyzer to a semiconductor manufacturing process, the reliability and the productivity of the resulting semiconductor devices can be improved.

BRIEF DESCRIPTION OF THE DRAWINGS

The above object and other advantages of the present invention will become more apparent by describing in detail preferred embodiments thereof with reference to the attached drawings in which:

FIG. 17 is a block view illustrating a fluid analyzer including the fluid sampling apparatus shown in FIG. 1 and a measuring apparatus.

DETAILED DESCRIPTION OF PREFERRED EMBODIMENTS

Hereinafter, the present invention will be described in detail with reference to accompanying drawings.

Figure 1:
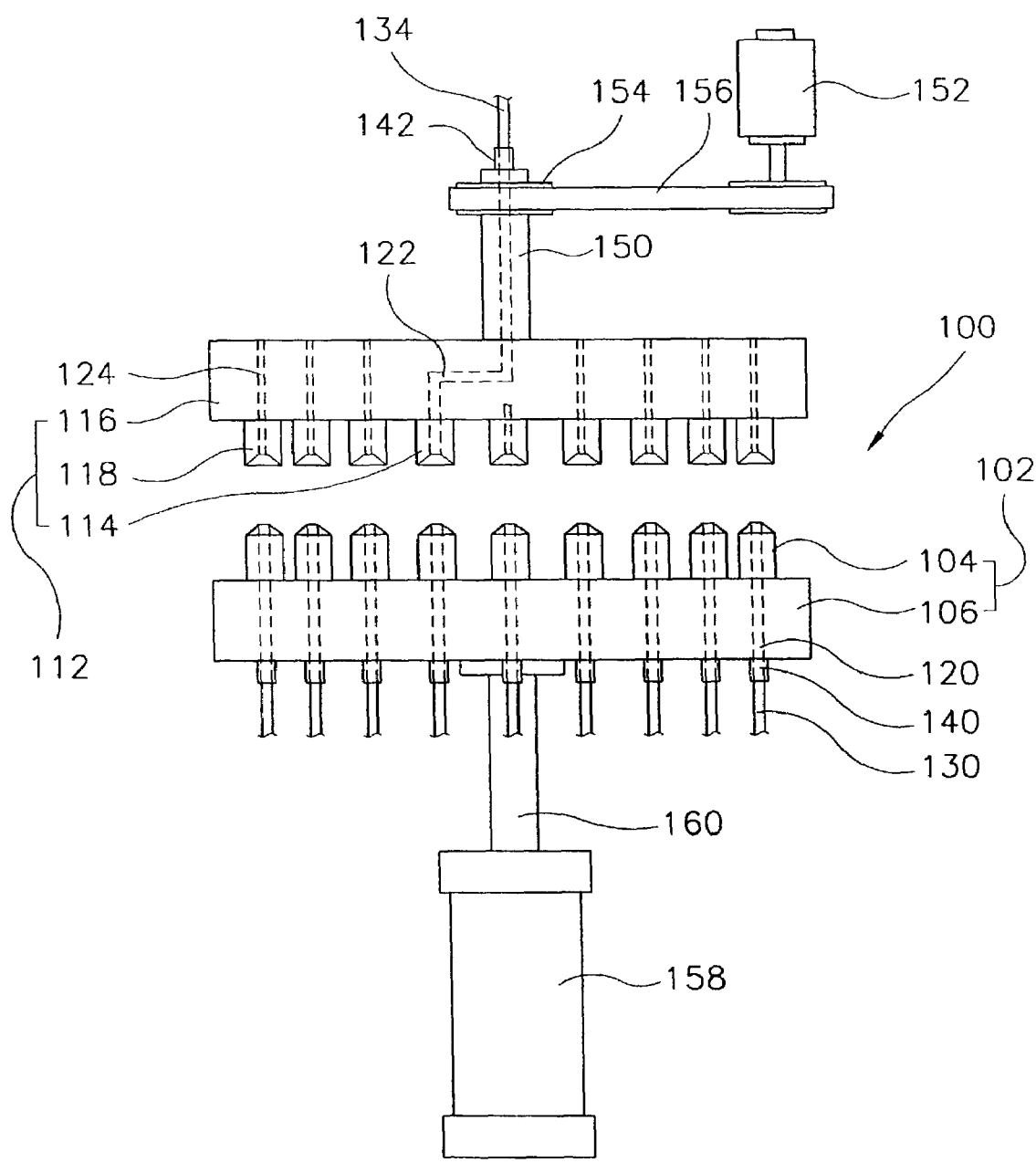
FIG. 1 is a schematic view showing a fluid sampling apparatus according to a first embodiment of the present invention.

FIG. 1 is a schematic view showing a fluid sampling apparatus according to a first embodiment of the present invention. Referring to FIG. 1, the fluid sampling apparatus 100 has a first nozzle assembly 102 including a plurality of outlet nozzles 104 connected to lines supplying process fluids into semiconductor manufacturing devices (not shown) and a first plate 106, on which the outlet nozzles 104 are installed. A plurality of first fluid passages 120 are formed in the first plate 106 by perforating the first plate 106 from an upper surface to a lower surface thereof. The first fluid passages 120 are arranged in a circular pattern with a predetermined interval. The outlet nozzles 104 are respectively connected to first sides of the first fluid passages 120 adjacent to the upper surface of the first plate 106. In addition, a plurality of sampling lines 130 are connected to second sides of the first fluid passages 120 through a plurality of first fittings 140.

A second nozzle assembly 112 is in opposition to the first nozzle assembly 102 so as to receive the process fluids from the first nozzle assembly 102. The second nozzle assembly 112 includes a second plate 116 positioned in opposition to the first plate 106 and an inlet nozzle 114 installed in the second plate 116 such that the inlet nozzle 114 faces outlet nozzles 104. The inlet nozzle 114 is connected to a measuring apparatus (not shown), which is provided to measure the contamination level of the process fluids supplied through the outlet nozzles 104. The fluid sampling apparatus 100 further includes a container (not shown) for receiving the first and second nozzle assemblies 102 and 112 therein. The first sampling lines 130 are provided in the container, and second sampling lines (not shown) are provided so as to connect the first sampling lines 130 to the lines supplying the process fluids into the semiconductor manufacturing devices, respectively.

A rotating shaft 150 is provided at a center of a second side of the second plate 116, which is opposite to the first side of the second plate 116 having the inlet nozzle 114. A motor 152 is connected to the rotating shaft 150 to provide a rotational force. The motor 152 and the rotating shaft 150 are connected to each other through two pulleys 154 and a timing belt 156. A central axis of the rotating shaft 150 is coaxially arranged with a center of a circle defined by the arrangement of the outlet nozzles 104. A distance between the rotating shaft 150 and the inlet nozzle 114 is identical to a radius of the circle defined by the arrangement of the outlet nozzles 104. That is, the trace of the inlet nozzle 114 moved by the rotation of the rotating shaft 150 is identical to the circle defined by the arrangement of the outlet nozzles 104. Accordingly, the rotating shaft 150 rotated by the operation of the motor 152 can selectively match the central axis of the inlet nozzle 114 with central axes of the outlet nozzles 104. Here, the motor 152 for providing the rotational force includes a step motor capable of adjusting the rotation angle of the rotating shaft.

A rod 160 of a pneumatic cylinder 158 is connected to a lower surface of the first plate 106 so as to connect or separate the outlet nozzle 104 to or from the inlet nozzle 114 of which the central axes align with each other by the operation of the motor 152. That is, the central axis of the inlet nozzle 114 is selectively matched with the central axis of one of the outlet nozzles 104 by the operation of the motor 152. In this state, the pneumatic cylinder 158 extends to connect the outlet nozzle 104 and the inlet nozzle 114. Therefore, the contamination level of the process fluids passing through the plurality of process fluid lines can be measured by repeatedly operating the motor 152 and the pneumatic cylinder 158.

When the selected outlet nozzle 104 is connected to the inlet nozzle 114 by the rotation of the motor 152 and the extension of the pneumatic cylinder 158, a rotational moment is applied to the first plate 106 since the connection point between the outlet nozzle 104 and the inlet nozzle 114 is offset from the position of the first plate 106 to which the force of the pneumatic cylinder 158 is applied. In order to solve the above problem, a plurality of auxiliary nozzles 118, which are respectively connected to the outlet nozzles 104 except for the selected outlet nozzle connected to the inlet nozzle 114, are provided in the second nozzle assembly 112. That is, the inlet nozzle 114 and the auxiliary inlet nozzles 118 are arranged at the first side of the second plate 116 in the same circular arrangement with the circular arrangement of the outlet nozzles 104 to compensate for the rotational moment.

A second fluid passage 122 is formed in the second plate 116. The second fluid passage 122 is connected to the inlet nozzle 114 and passes through a center axis of the rotating shaft 150. A second fitting 142 is provided for connecting a third sampling line 134 to the measuring apparatus at one end of the second fluid passage 122 formed at one end of the rotating shaft 150. A plurality of third fluid passages 124 are formed in the second plate 116 passing through the second plate 116. The auxiliary inlet nozzles 118 are connected to first ends of the third fluid passages 124. The width of the third fluid passage 124 is formed to be smaller than the width of the second fluid passage 122. The reason behind forming the third fluid passages 124 and the reason for the difference in widths between the second fluid passage 122 and the third fluid passages 124 is explained in detail below.

Figure 2:
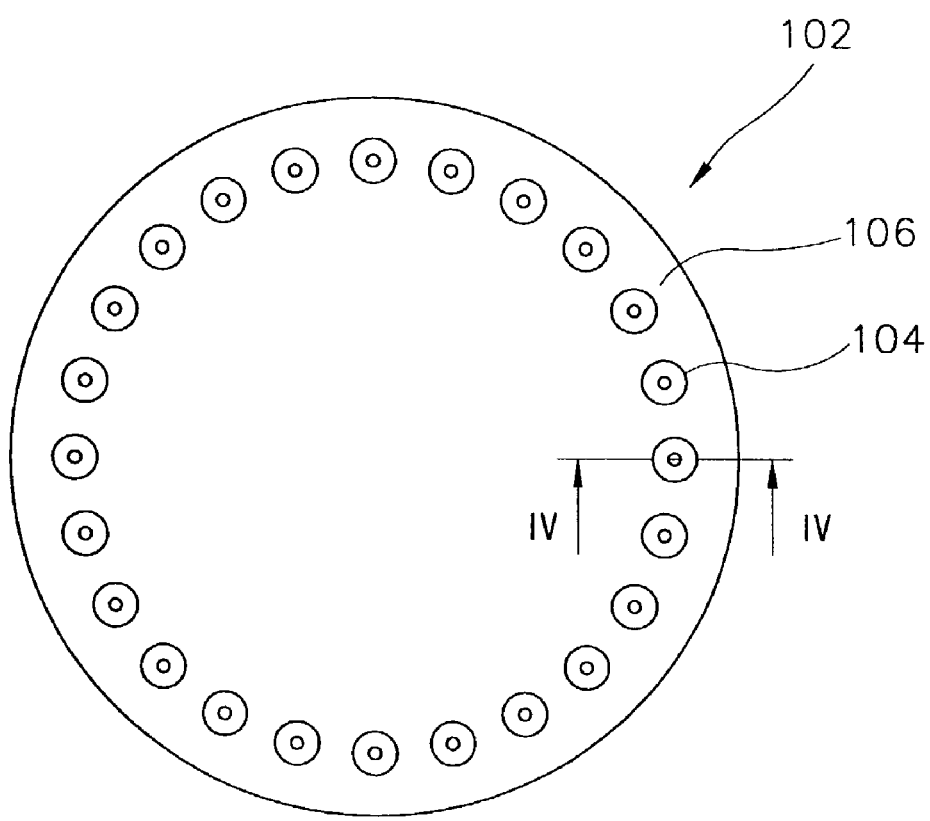
FIG. 2 is a plan view showing a first nozzle assembly shown in FIG. 1.
Figure 3:
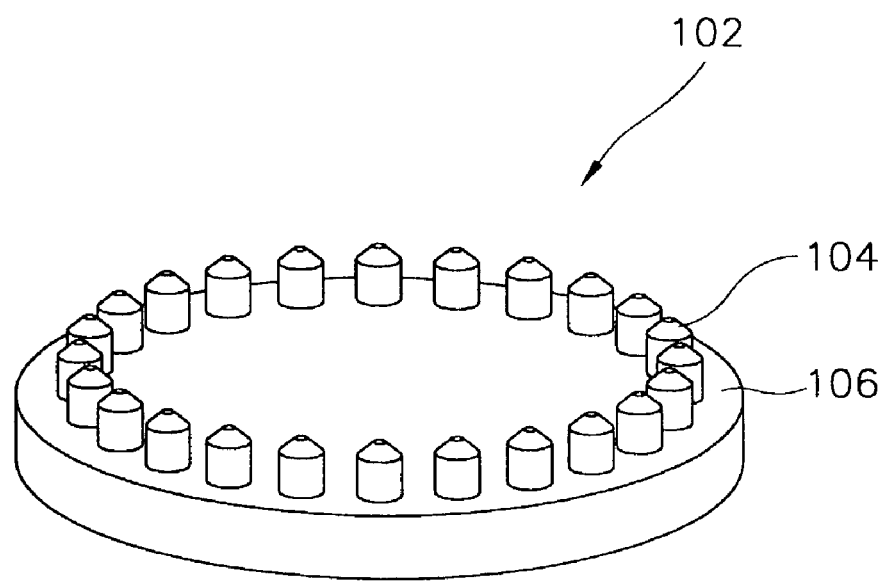
FIG. 3 is a perspective view showing a first nozzle assembly shown in FIG. 1.

FIG. 2 is a plan view showing the first nozzle assembly shown in FIG. 1, and FIG. 3 is a perspective view showing the first nozzle assembly shown in FIG. 1. In addition, FIG. 4 is a sectional view taken along the line IV—IV in FIG. 2.

Figure 4:
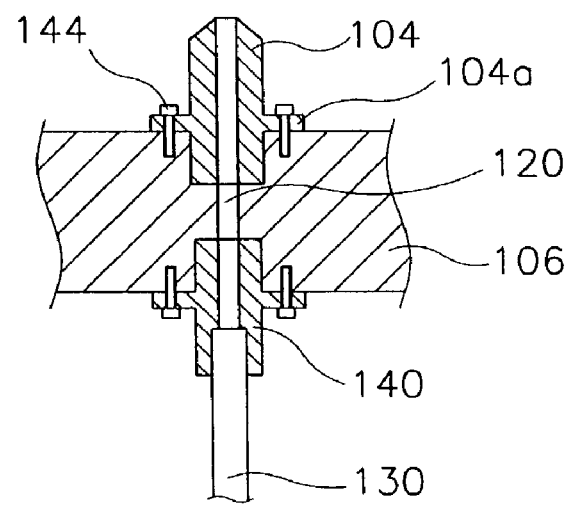
FIG. 4 is a sectional view taken along the line IV—IV in FIG. 2.

Referring to FIGS. 2 to 4, the first nozzle assembly 102 includes the first plate 106 and outlet nozzles 104. The first plate 106 has a disc shape. The outlet nozzles 104 are arranged at a periphery of the first plate 106 in a circumferential direction thereof at predetermined intervals. First protrusions 104a are formed at flank portions of the outlet nozzles 104 so as to fix the outlet nozzles 104 to the first plate 106. The first protrusion 104a is formed with a plurality of first perforation holes in parallel to the central axis of the outlet nozzle 104.

The first plate 106 is formed with the first fluid passages 120 connected to the outlet nozzles 104, and stepped portions are formed at both ends of the first fluid passages 120 so as to fix the outlet nozzle 104 and the first fitting 140 to the first plate 106, respectively. In addition, a plurality of first screw holes are formed at a periphery of the first fluid passage 120 corresponding to the first perforation holes formed in the first protrusion 104a. The outlet nozzle 104 is fixed to the first plate 106 by a plurality of bolts 144.

Though twenty-four outlet nozzles 104 are illustrated in figures, the number of the outlet nozzles 104 can be varied in the present invention. In addition, the first fitting 140 for connecting the first sampling line 130 to the first passage 120 is fixed to the first plate 106 in the similar manner as the outlet nozzle 104.

Figure 5:
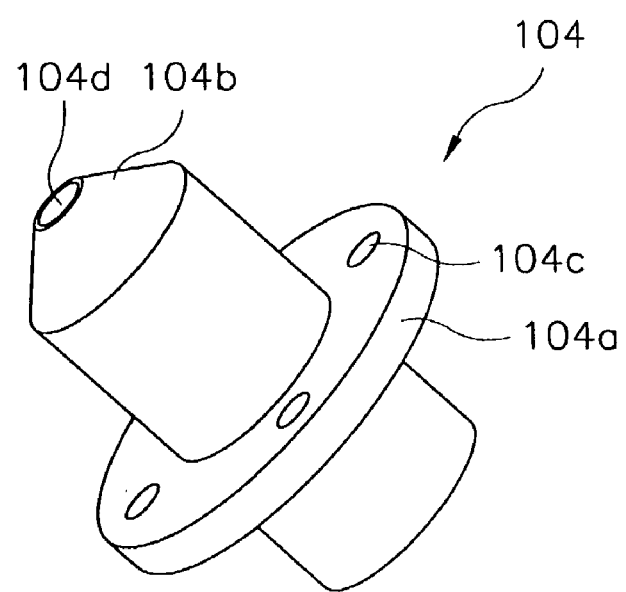
FIG. 5 is a perspective view showing an outlet nozzle shown in FIG. 1.

FIG. 5 is a perspective view of the outlet nozzle shown in FIG. 1.

Referring to FIG. 5, one end 104b of the outlet nozzle 104 is protruded in an axial direction with a conical shape. The first protrusion 104a is formed at the flank portion of the outlet nozzle 104 for fixing the outlet nozzle 104 to the first plate 106. In addition, the first protrusion 104a is formed with plural first perforation holes 104c in parallel to the central axis of the outlet nozzle 104. The outlet nozzle 104 is formed at a central axis thereof with a second perforation hole 104d connected to the first fluid passage 120 of the first plate 106. The reason for forming one end 104b of the outlet nozzle 104 in the conical shape is to reduce the spraying angle of the process fluid that is sprayed through the outlet nozzle 104. That is, when the outlet nozzle 104 is connected to the inlet nozzle 114 (refer to FIG. 1), the conical shaped end 104b of the outlet nozzle 104 reduces the resistance caused by the process fluid and facilitates the flow of the process fluid.

Figure 6:
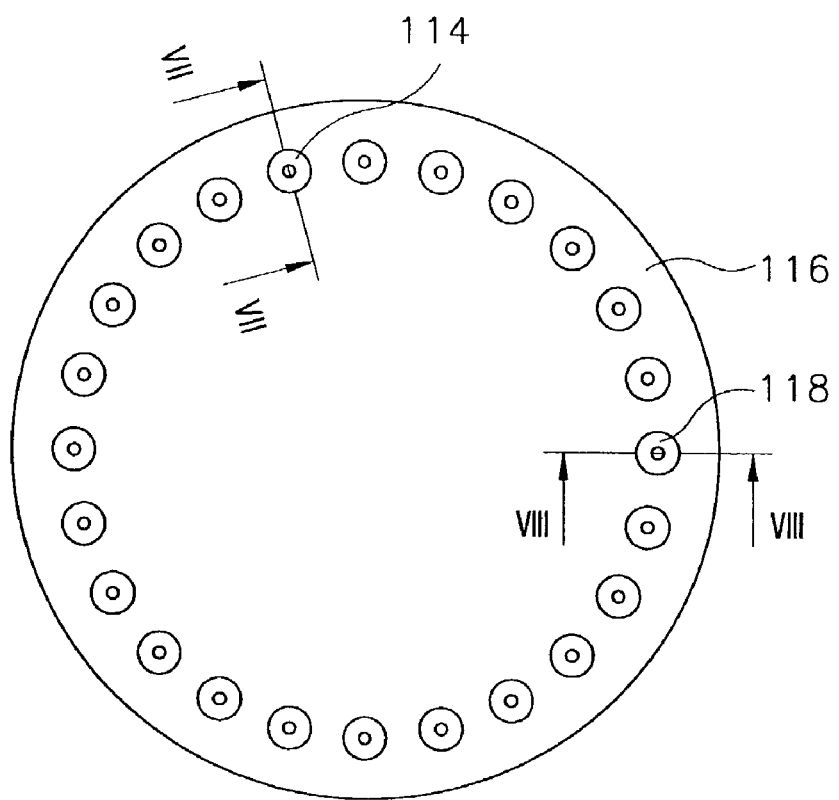
FIG. 6 is a plan view showing a second nozzle assembly shown in FIG. 1.
Figure 7:
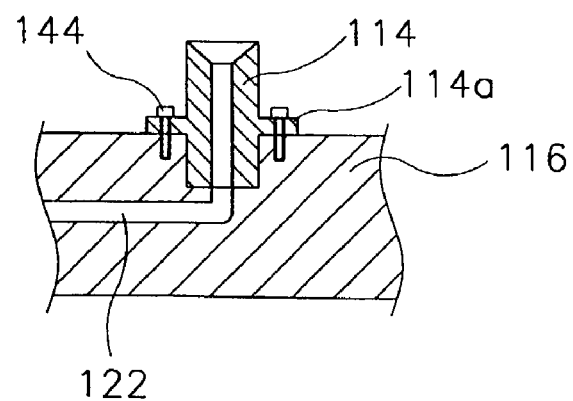
FIG. 7 is a sectional view taken along the line VII—VII in FIG. 6.

FIG. 6 is a plan view of the second nozzle assembly shown in FIG. 1. FIG. 7 is a sectional view taken along the line VII—VII in FIG. 6 and FIG. 8 is a sectional view taken along the line VIII—VIII in FIG. 6.

Figure 8:
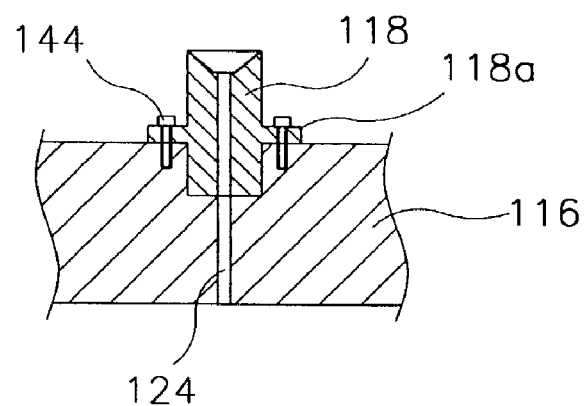
FIG. 8 is a sectional view taken along the line VIII—VIII in FIG. 6.

Referring to FIGS. 6 to 8, the second nozzle assembly 112 includes the second plate 116, the inlet nozzle 114 and plural auxiliary inlet nozzles 118. The second plate 116 has a disc shape with a size corresponding to a size of the first plate 106 shown in FIG. 2. In addition, the inlet nozzle 114 and the auxiliary inlet nozzles 118 are arranged similar to the outlet nozzles 104 arranged on the first plate 106 (referred to FIG. 2). in a similar manner to the outlet nozzles 104, the inlet nozzle 114 and the auxiliary inlet nozzles 118 are formed at flank portions thereof with second and third protrusions 114a and 118a, respectively. The second protrusion 114a is formed with a plurality of third perforation holes in parallel to the center central axis of the inlet nozzle for fixing the inlet nozzle 114 to the second plate 116. In addition, a plurality of second screw holes corresponding to the third perforation holes are formed at a periphery of the second fluid passage 122. The inlet nozzle 114 is fixed to the second plate 116 by bolts 144.

The second fluid passage 122 connected to the inlet nozzle 114 extends to a central portion of the second side of the second plate 116 by passing through the second plate 116. The third fluid passages 124 connected to the auxiliary inlet nozzles 118 extend from the first side to the second side of the second plate 116 by passing through the second plate 116. At this time, the cross-sectional area of the third fluid passage 124 is formed smaller than the cross-sectional area of the second fluid passage 122. Preferably, the ratio of cross-sectional area of the second fluid passage 122 to the sectional area of the third fluid passage is approximately 2:1 so as to reduce the loss of process fluids. In detail, the process fluids are continuously supplied through the first sampling lines 130 (see FIG. 1), the first fluid passages 120 and the outlet nozzles 104. When the inlet nozzle 114 is connected to the selected outlet nozzle 104, remaining outlet nozzles 104 are respectively connected to the auxiliary inlet nozzles 118, and the process fluids flow through the third fluid passages 124 having the sectional area smaller than that of the second fluid passage 122. The reason for continuously flowing the process fluids is to prevent the process fluids from staying dormant in the first sampling lines 130. That is, the process fluids remaining dormant in the first sampling lines 130 can themselves become contaminated in the first sampling lines 130, thereby interrupting the precise measurement of contamination. Therefore, it is preferred for the measurement to allow the process fluids to continuously flow and to reduce the sectional area of the third fluid passage 124 for reducing loss of the process fluids. The drainage of the process fluids continuously flowing through the auxiliary inlet nozzles 118 and the third fluid passage 124 will be explained below.

Figure 9:
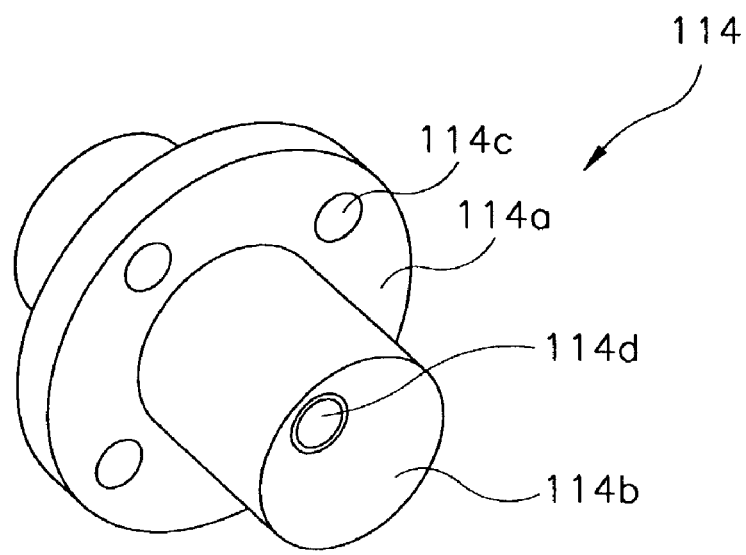
FIG. 9 is a perspective view showing an inlet nozzle shown in FIG. 1.

FIG. 9 is a perspective view of the inlet nozzle shown in FIG. 1.

Referring to FIG. 9, one end 114b of the inlet nozzle 114 connected to the outlet nozzle 104 (referred to FIG. 5) is concave in a reverse-conical shape corresponding to the conical end 104b of the outlet nozzle 104. That is, when the outlet nozzle 104 is connected to the inlet nozzle 114, end 104b of the outlet nozzle 104 makes contact with end 114b of the inlet nozzle 114.

In addition, a second protrusion 114a is formed at flank portion of the inlet nozzle 114. The second protrusion 114a is formed with a plurality of third perforation holes 114c, which are arranged in parallel to the center central axis of the inlet nozzle 114 for fixing the inlet nozzle 114 to the second plate 116. In addition, a fourth perforation hole 114d is formed along the center axis of the inlet nozzle 114 for allowing the process fluids to flow therethrough. At this time, the shape of the auxiliary nozzle 118 (referred to FIG. 8) is similar to the shape of the inlet nozzle 114, and the diameter of the perforation hole formed along the center axis of the auxiliary nozzle 118 is smaller than that of the inlet nozzle 114.

Figure 10:
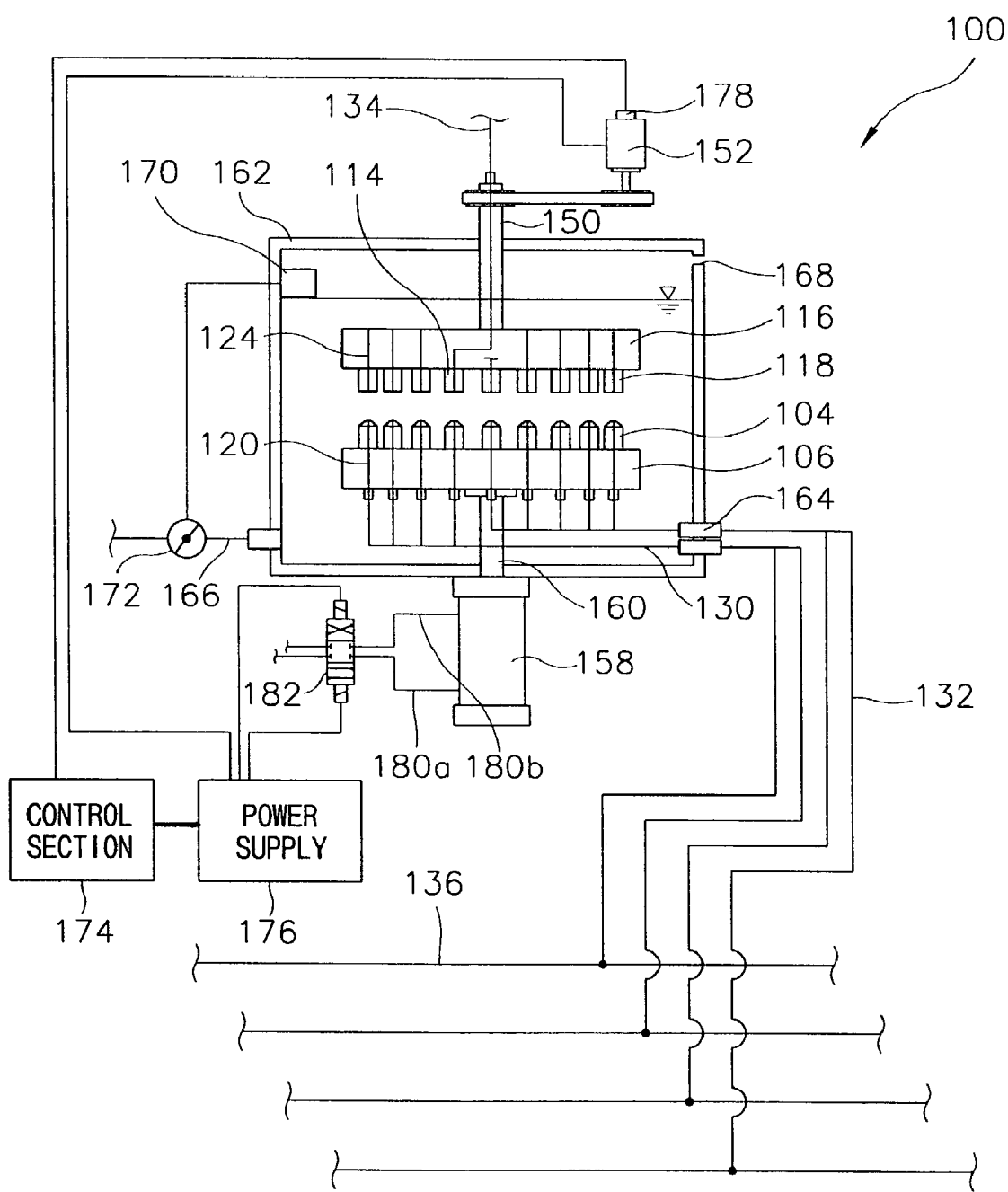
FIG. 10 is a schematic view of an apparatus for sampling deionized water by using the fluid sampling apparatus shown in FIG. 1.

FIG. 10 is a schematic view for illustrating an apparatus for sampling deionized water by using the fluid sampling apparatus shown in FIG. 1. Referring to FIG. 10, an enclosed container 162 has the first plate 106 connected to the outlet nozzles 104 and the second plate 116 connected to the inlet nozzle 114 and auxiliary inlet nozzles 118 therein. The pneumatic cylinder 158 is connected to a lower side of the enclosed container 162. The rod 160 of the pneumatic cylinder 158 extends into the enclosed container 162 passing through the enclosed container 162 and is connected to a lower surface of the first plate 106. The step motor 152 is provided on the enclosed container 162 and the rotating shaft 150 connected to the step motor 152 extends into the enclosed container 162 and is connected an upper surface of the second plate 116.

A plurality of connectors 164 for connecting the first sampling lines 130 to the second sampling lines 132 are provided at a side portion of the enclosed container 162. The second sampling lines 132 are connected to deionized water supplying lines 136, which supply deionized water to semiconductor manufacturing devices. Sampling points of deionized water are marked in the connectors 164. That is, identification numbers of the deionized water supplying lines 136 are marked in the connectors 164.

When the fluid sampling apparatus is initially set, deionized water is filled in the container 162 through the outlet nozzles 104. When the first and second plates 106 and 116 are sufficiently immersed in deionized water supplied into the container 162, deionized water supplied into the container 162 is discharged through a drain line 166 connected to another side portion of the container 162. In addition, an exhaust port 168 is formed at an upper sidewall of the container for exhausting air contained in the container 162. A water level detecting sensor 170 is installed in the container 162 for detecting the level of deionized water, and a valve 172 operated based on a signal from the water level detecting sensor 170 is installed in the drain line 166. The valve 172 allows deionized water to be constantly maintained at a predetermined level. Various forms of water level detecting sensors are applicable to the present invention. In addition, various types of valves, including a solenoid valve, can be installed in the drain line 166.

The fluid sampling apparatus 100 includes a control section 174, which controls the operation of the step motor 152 in order to select one of outlet nozzles 104. The control section 174 is connected to a power supply 176 so as to send the operating signal of the step motor 152 to the power supply 176. The power supply 176 supplies the power to the step motor 152 based on the signal from the control section 174, and the step motor 152 is operated upon receiving the power. An encoder 178 for detecting the rotational angle of the rotating shaft 150 is provided at one side of the step motor 152. The rotational angle detecting signal of the encoder 178 is transmitted to the control section 174. The control section 174 generates a control signal based on the rotational angle detecting signal of the encoder 178. That is, by performing feedback control utilizing the rotational angle detecting signal of the encoder 178 and the control signal of the control section 174, the central axis of the selected outlet nozzle 104 can be precisely matched with the central axis of the inlet nozzle 114.

In addition, the control section 174 controls the operation of the pneumatic cylinder 158 to reciprocate the first plate 106. The rod 160 of the pneumatic cylinder 158 is connected to the lower surface of the first plate 106 and connects the selected outlet nozzle 104 to the inlet nozzle 114, after the central axes of the selected outlet nozzle 104 and the inlet nozzle 114 are matched with each other by the step motor 152. The pneumatic cylinder 158 is operated with pressurized air and the flow of pressurized air is controlled by the control section 174. That is, pressurized air lines 180a and 180b connected to the pneumatic cylinder 158 are connected to a directional control valve 182 and the directional control valve 182 is opened/closed by a solenoid. The control section 174 transmits the operating signal of the pneumatic cylinder 158 to the power supply 176 and the power supply 176 supplies the power to the solenoid of the directional control valve 182 based on the operating signal of the pneumatic cylinder 158. The pneumatic cylinder 158 may include, for example, a single-acting cylinder or a double-acting cylinder. Accordingly, the type of directional control valve 182 can be varied to match the operation of the pneumatic cylinder 158.

When the outlet nozzle selected from the plural outlet nozzles 104 is connected to the inlet nozzle 114 by the operation of the step motor 152 and the pneumatic cylinder 158, remaining outlet nozzles 104 are connected to the auxiliary inlet nozzles 118. Deionized water supplied through the selected outlet nozzle 104 is introduced into the measuring apparatus (not shown) through the inlet nozzle 114, and remaining deionized water is supplied into the container 162 through the auxiliary inlet nozzles 118. At this time, since the auxiliary inlet nozzles 118 are connected to the third fluid passage 124 of the second plate 116, the loss of deionized water can be minimized by forming the sectional area of the third fluid passage 124 to be relatively small in size. At this time, the flow rate of deionized water supplied into the container 162 through the third fluid passage 124 is reduced as compared with the case when the outlet nozzles 104 are separated from the inlet nozzle 114 and auxiliary inlet nozzles 118. Therefore, the water level in the container 162 is changed. The water level detecting sensor 170 installed in the container 162 detects the change of the water level in the container 162. In response the degree of opening of the valve 172 is adjusted based on the signal from the water level detecting sensor 170. From an economic standpoint, it is preferred that the deionized water is reused so as to be continuously discharged by properly treating the discharged deionized water.

The continuous discharge of deionized water operates to wash elements located in the container 162, such as the first and second plates 106 and 116, thereby reducing the risk of contamination of the deionized water caused by the fluid sampling apparatus 100. In addition, since the outlet nozzle 104 is connected to or separated from the inlet nozzle 114 while being immersed in deionized water, impurities cannot be introduced through the inlet nozzle 114. Therefore, the reliability of the measuring apparatus for the contamination level measurement can be improved.

On the other hand, a gas sampling work can be achieved by using a fluid sampling apparatus having the structure similar to the structure of the fluid sampling apparatus shown in FIG. 10. In this case, a pressure sensor is provided in the container 162 instead of the water level detecting sensor 170. In addition, the exhaust port 168, which is required to exhaust air from the container 162 when sampling deionized water, is not needed. That is, in this case, the interior of the container 162 is sealed from the exterior of the container 162 during a gas sampling operation. The type of gas can vary, for example, air, nitrogen, oxygen or argon. It is possible to use a pressure control valve instead of the pressure sensor and the valve 172 installed in the drain line 166. The pressure control valve is opened when an internal pressure of the container 162 exceeds a predetermined pressure level, thereby controlling the internal pressure of the container 162. The pressure control valve can be also used when sampling deionized water.

The distance of the outlet nozzles 104 from the inlet nozzle 114 or from the auxiliary inlet nozzles 118 can be varied depending on the pressure of the process fluids and inner diameters of the nozzles. In the case of deionized water, the pressure of the deionized water to be supplied is, for example, about 3 to 6 kg/cm$^2$. For example, in the case where the inner diameter of the outlet nozzle 104 is ¼ inch, the distance between the outlet nozzle and the inlet nozzle 114 or auxiliary nozzles 118 is preferably about 5 to 10 mm. If the distance is larger than the above range, deionized water emitted from the outlet nozzles 104 cannot effectively wash the inlet nozzle 114 and auxiliary nozzles 118. If the distance is smaller than the above range, deionized water emitted from the outlet nozzles 104 disturbs the operation for matching the central axes of the outlet nozzle 104 and the inlet nozzle 114. The above-stated range is also adapted the case where sampling gases are to be sampled.

The outlet nozzles 104 for supplying the process fluids, the inlet nozzle 114 for sampling the process fluids, and the auxiliary nozzles 118 for reducing the loss of the process fluids and for allowing the selected outlet nozzle 104 to be stably connected to the inlet nozzle 114 are preferably composed of a material having superior durability and corrosion resistance. According to the first embodiment of the present invention, Teflon™ is preferably used for the nozzle material. However, other materials can be used if they satisfy the above requirements. The first and second plates 106 and 116 are preferably also made of Teflon™. However, since driving forces of the step motor 152 and the pneumatic cylinder 158 are applied to the first and second plates 106 and 116, a material having a superior strength, such as stainless steel, can be used for the first and second plates 106 and 116.

On the other hand, the first sampling lines 130 connected to the first fluid passages 120 formed in the first plate 106 in the container 162 are preferably composed of a flexible material, since they are connected to the first plate 106 reciprocated by the pneumatic cylinder 158. Similarly, since the third sampling line 134 connected to one end of the rotating shaft 150 is subject to a twisting force by the rotation of the rotating shaft 150, the third sampling line 134 is preferably made of flexible material. At this time, a rotational valve for supplying the fluid to a rotating object can be adopted for the third sampling line 134. However, if the rotational valve is adopted, the process fluids can be contaminated while passing through the rotation valve. Accordingly, it is preferred to use the third sampling line 134 made of flexible material, while limiting the rotational angle of the rotating shaft 150 to 360°.

Figure 11:
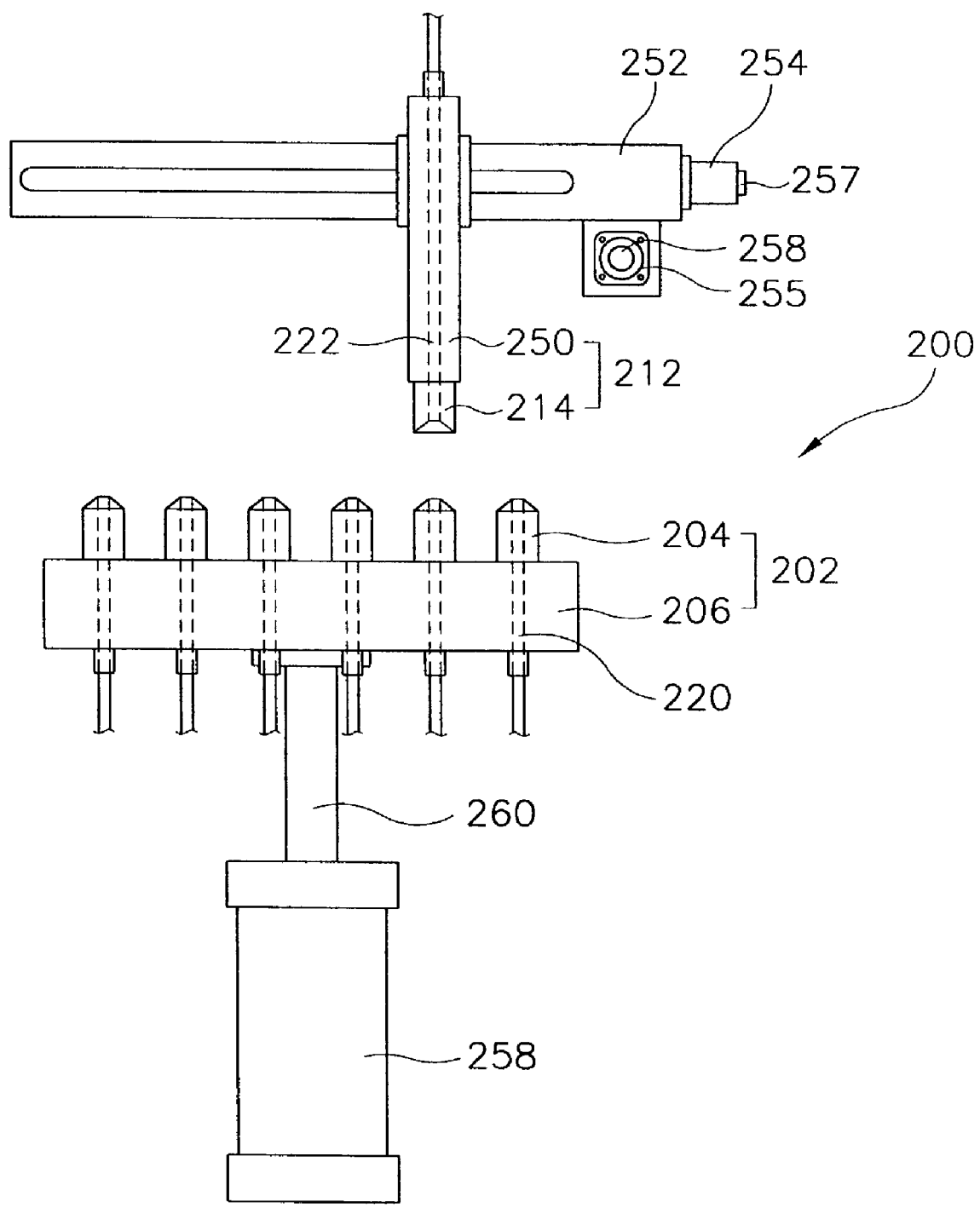
FIG. 11 is a schematic view showing a fluid sampling apparatus according to a second embodiment of the present invention.

FIG. 11 is a schematic view showing a fluid sampling apparatus according to a second embodiment of the present invention.

Referring to FIG. 11, the fluid sampling apparatus 200 according to the second embodiment of the present invention has a first nozzle assembly 202 including a plurality of outlet nozzles 204 and a plate 206. The outlet nozzles 204 are installed on an upper surface of the plate 206. The plate 206 is a flat plate having a rectangular shape, and the outlet nozzles 204 are arranged in a rectangular pattern. A rod 260 of a pneumatic cylinder 258 is connected to a lower surface of the plate 206 so as to vertically reciprocate the plate 206.

A second nozzle assembly 212 having an inlet nozzle 214 connected to an outlet nozzle selected from the plural outlet nozzles 204 is installed above the plate 206. The second nozzle assembly 212 includes a connection member 250 for connecting the inlet nozzle 214 to a 2-axis Cartesian coordinate robot 252. The connection member 250 has a rectangular bar shape and is installed at one end thereof with the inlet nozzle 214.

A plurality of first fluid passages 220 are formed in the plate 206 by vertically passing through the plate 206. The outlet nozzles 204 are connected to first sides of the first fluid passages 220 adjacent to the upper surface of the plate 206. The connecting method and the shape of the outlet nozzles 204 are identical to those of the first embodiment, so a detailed description thereof will be omitted. The connection member 250 for connecting the inlet nozzle 214 to the 2-axis Cartesian coordinate robot 252 is vertically installed and a second fluid passage 222 is formed in the connection member 250 by vertically passing through a central portion of the connection member 250. In addition, the inlet nozzle 214 is connected to the lower end of the connection member 250. The shape of the inlet nozzle 214 is identical to the shape of the inlet nozzle 114 of the first embodiment.

The 2-axis Cartesian coordinate robot 252 includes two motors 254 and 255. The first motor 254 provides a driving force in an X-axis direction, and the second motor 255 provides a driving force in a Y-axis direction. Lead screws (not shown) accommodated in the 2-axis Cartesian coordinate robot 252 are connected to rotating shafts of the first and second motors 254 and 255. The 2-axis Cartesian coordinate robot 252 is driven by the rotation of the lead screws. First and second encoders 257 and 258 are respectively connected to first sides of the first and second motors 254 and 255 so as to detect the rotational angle of the rotating shafts. That is, the 2-axis Cartesian coordinate robot 252 moves the position of the inlet nozzle 214 based on predetermined coordinates.

After a central axis of the inlet nozzle 214 has been matched with a central axis of one outlet nozzle 204 selected from the plural outlet nozzles 204 by the operation of the 2-axis Cartesian coordinate robot 252, the pneumatic cylinder 258 extends so that the selected outlet nozzle 204 is connected to the inlet nozzle 214. At this time, in the same manner as the first embodiment, the process fluids are continuously supplied through the plural outlet nozzles 204.

Figure 12:
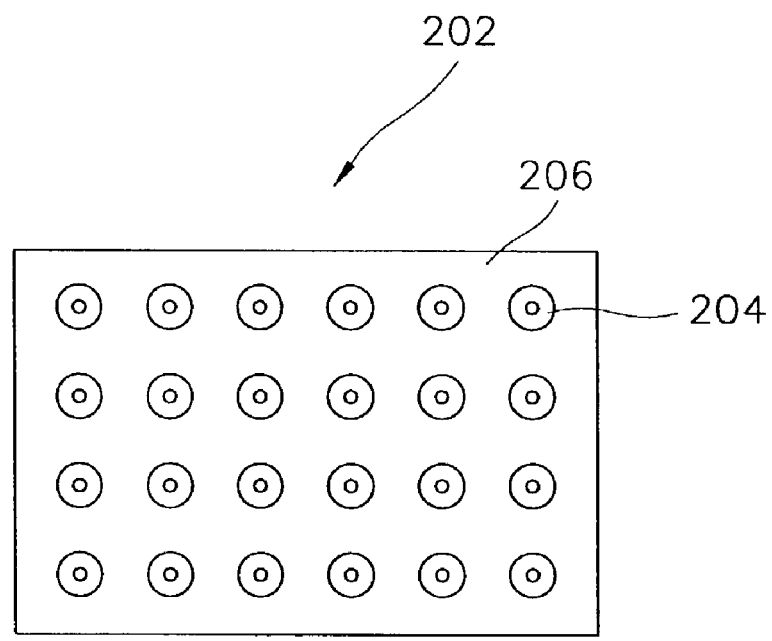
FIG. 12 is a plan view showing a first nozzle assembly shown in FIG. 11.
Figure 13:
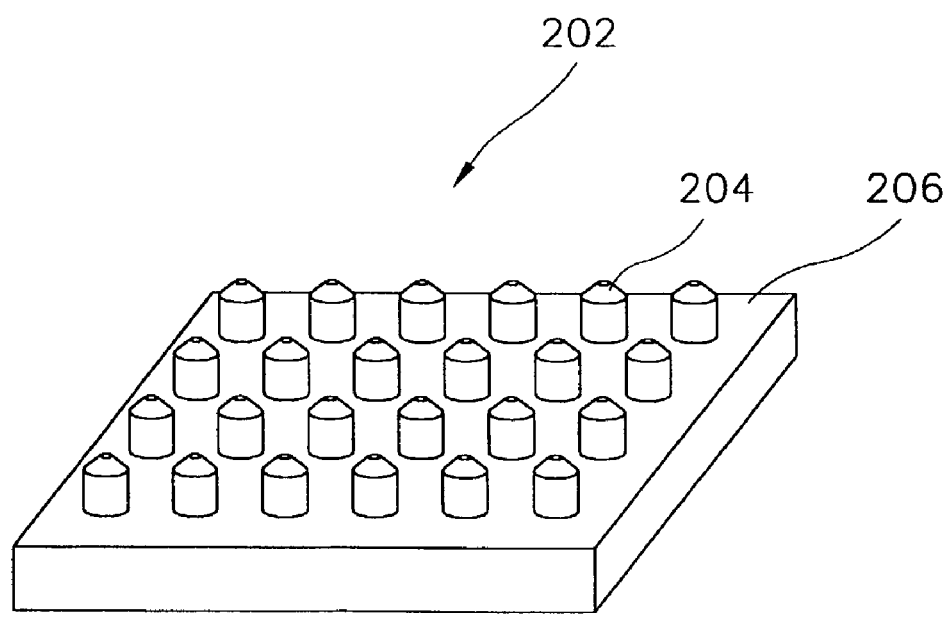
FIG. 13 is a perspective view showing a first nozzle assembly shown in FIG. 11.

FIG. 12 is a plan view of the first nozzle assembly shown in FIG. 11, and FIG. 13 is a perspective view of the first nozzle assembly shown in FIG. 11.

Referring to FIGS. 12 and 13, the first nozzle assembly 202 includes plural outlet nozzles 204 and the plate 206. The plate 206 is a rectangular flat plate and the outlet nozzles 204 are arranged on the upper surface of the plate 206 in a rectangular pattern. Twenty-four outlet nozzles 204 are arranged in a 4×6 matrix form.

Figure 14:
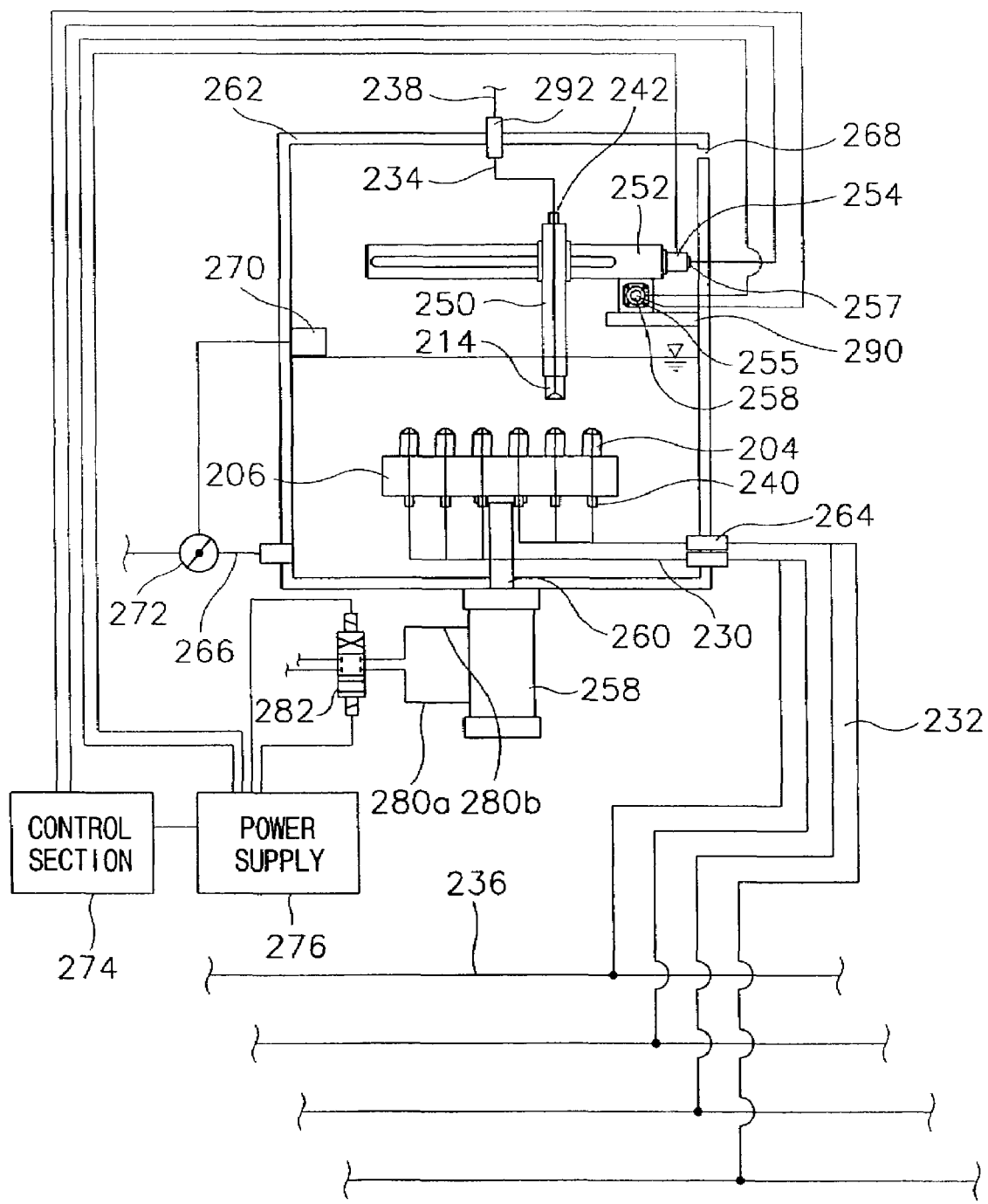
FIG. 14 is a schematic view for explaining an apparatus for sampling deionized water by using a fluid sampling apparatus shown in FIG. 11.

FIG. 14 is a schematic view for explaining an apparatus for sampling deionized water by using the fluid sampling apparatus shown in FIG. 11.

Referring to FIG. 14, the fluid sampling apparatus 200 has a container 262 for accommodating the first and second nozzle assemblies 202 and 214 and the 2-axis Cartesian coordinate robot 252. A plurality of first connectors 264 are installed by passing through one sidewall of the container 262 so as to couple the first sampling lines 230 connected to the plate 206 to the second sampling lines 232 connected to deionized water supplying lines 236, which supply deionized water to semiconductor manufacturing devices. The 2-axis Cartesian coordinate robot 252 is installed on a bracket 290 provided at an inner upper sidewall of the container 262, and the connection member 250 for connecting the inlet nozzle 214 is connected to the 2-axis Cartesian coordinate robot 252. One end of a third sampling line 234 is connected to an upper end of the connection member 250 and the other end thereof is connected to a second connector 292, which is installed by passing through a ceiling of the container 262. In addition, a fourth sampling line 238 connected to the measuring apparatus for measuring the contamination level of deionized water is coupled to the second connector 292 from an exterior of the container 262. The first sampling lines 230 are connected to the plate 206 through a plurality of first fittings 240, and the third sampling line 234 is connected to the connection member 250 through a second fitting 242. In addition, the pneumatic cylinder 258 is connected to the lower surface of the container 262 and the rod 260 of the pneumatic cylinder 258 extends into the interior of the container 262. A control section 274 and a power supply 276 similar to those of the first embodiment are provided.

A water level detecting sensor 270 is installed in the container 262 and a valve 272 opened/closed upon receiving the signal from the water level detecting sensor 270 is installed in a drain line 266 for discharging deionized water. The control section 272 controls the operation of the 2-axis Cartesian coordinate robot 252 and the pneumatic cylinder 258. The control section 274 is connected to the power supply 276. The power supply 276 supplies the power to the 2-axis Cartesian coordinate robot 252 and a directional control valve 282, which is installed in pressurized air lines 280a and 280b for supplying pressurized air to the pneumatic cylinder 258, based on the control signal of the control section 274. In addition, the control section 274 is connected to first and second encoders 257 and 258 coupled to the first and second motors 254 and 255 of the 2-axis Cartesian coordinate robot 252.

Hereinafter, the operation of the fluid sampling apparatus according to the second embodiment of the present invention will be described.

Firstly, deionized water is supplied into the container 262 through plural outlet nozzles 204 connected to the first sampling lines 230. When the level of deionized water in the container 262 reaches a predetermined level of the wafer level detecting sensor 270, the valve 272 installed in the drain line 266 is opened, so an amount of deionized water, which is identical to the flow rate of deionized water to be supplied, is discharged through the drain line 266. At this time, air contained in the container 262 is exhausted through an exhaust port 268 formed at an upper sidewall of the container 262.

Then, the control section 274 sends the control signal corresponding to a coordinate for moving the 2-axis Cartesian coordinate robot 252 to the power supply 276. Upon receiving the control signal, the power supply 276 supplies the power to the 2-axis Cartesian coordinate robot 252 so that the 2-axis Cartesian coordinate robot 252 matches the central axis of the inlet nozzle 214 with the central axis of the outlet nozzle 204 selected from plural outlet nozzles 204. At this time, the control section 274 controls the operation of the first and second motors 254 and 255 in real time based on the rotational angle detecting signal applied from the first and second encoders 257 and 258 until the central axis of the inlet nozzle 214 is precisely matched with the central axis of the selected outlet nozzle 204.

Next, the control section 274 generates a control signal for extending the rod 260 of the pneumatic cylinder 258, and the power supply 276 supplies the power to the solenoid of the directional control valve 282 based on the control signal of the control section 274. Accordingly, the pressurized air is supplied to the pneumatic cylinder 258 through the directional control valve 282, so the rod 260 of the pneumatic cylinder 258 is extended, thereby connecting the selected outlet nozzle 204 to the inlet nozzle 214.

In an alternative embodiment, sampling gases including air, nitrogen, oxygen, or argon, can be employed instead of fluids. In this case, a pressure sensor is installed in the container 262 instead of the water level detecting sensor 270. The gas sampling method is identical in operation to the deionized water sampling method.

Figure 15:
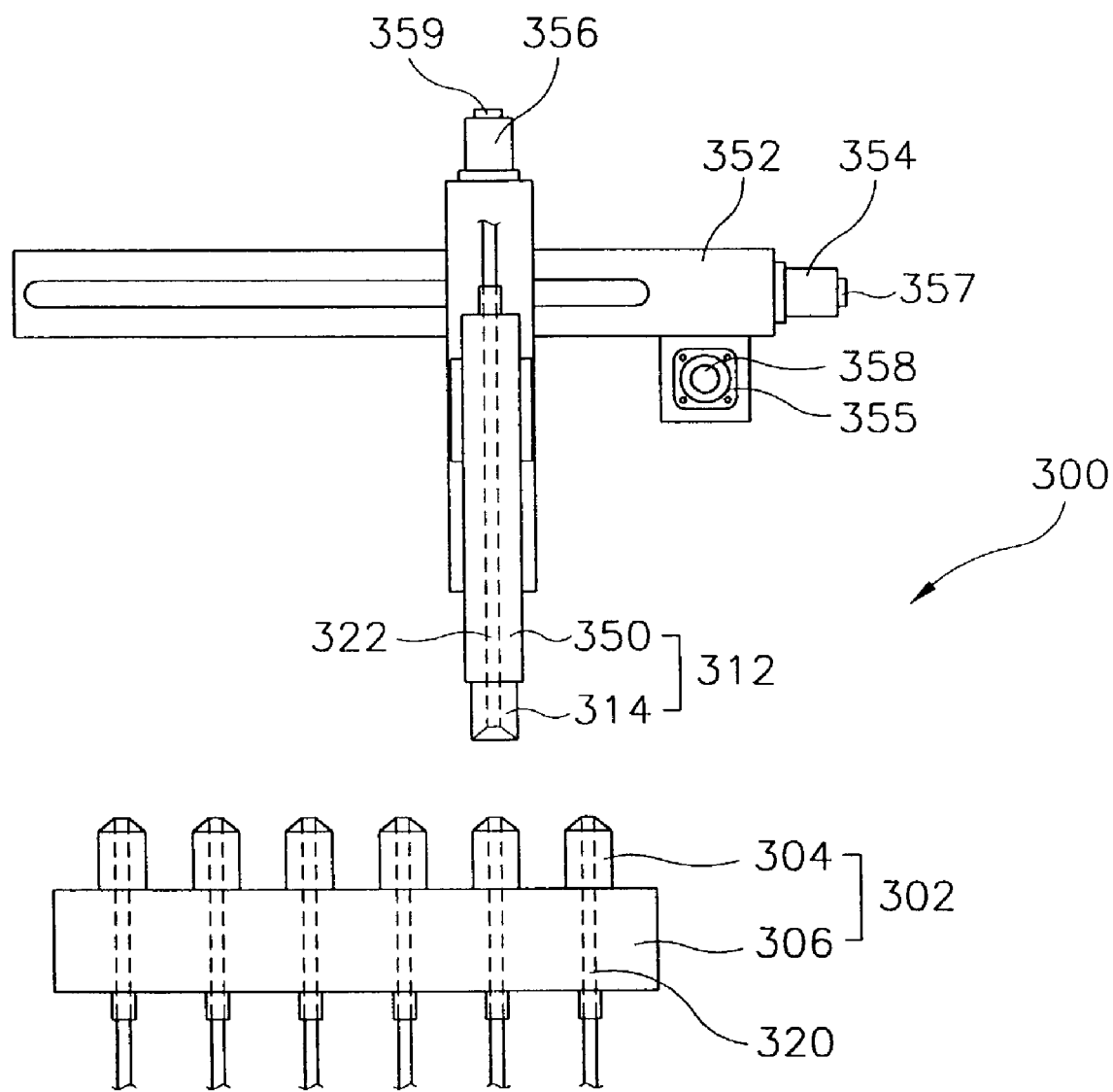
FIG. 15 is a schematic view showing a fluid sampling apparatus according to a third embodiment of the present invention.

FIG. 15 is a schematic view of a fluid sampling apparatus according to a third embodiment of the present invention.

Referring to FIG. 15, the fluid sampling apparatus 300 according to the third embodiment of the present invention has a first nozzle assembly 302 including a plurality of outlet nozzles 304 and a plate 306. The outlet nozzles 304 are installed on an upper surface of the plate 306. The plate 206 is a flat plate having a rectangular shape, and the outlet nozzles 204 are arranged in a rectangular pattern.

A second nozzle assembly 312 having an inlet nozzle 314 connected to an outlet nozzle selected from the plural outlet nozzles 304 is installed above the plate 306. The second nozzle assembly 312 includes a connection member 350 for connecting the inlet nozzle 314 to a 3-axis Cartesian coordinate robot 352. The connection member 350 has a rectangular bar shape and is installed at one end thereof with the inlet nozzle 314.

A plurality of first fluid passages 320 are formed in the plate 306 by vertically passing through the plate 306. The outlet nozzles 304 are connected to first sides of the first fluid passages 320 adjacent to the upper surface of the plate 306. The connecting method and the shape of the outlet nozzles 304 are identical to those of the first embodiment, so a detailed description thereof will be omitted. The connection member 350 for connecting the inlet nozzle 314 to the 3-axis Cartesian coordinate robot 352 is vertically installed and a second fluid passage 322 is formed in the connection member 350 by vertically passing through a central portion of the connection member 350. In addition, the inlet nozzle 314 is connected to the lower end of the connection member 350. The shape of the inlet nozzle 314 is identical to the shape of the inlet nozzle 114 of the first embodiment.

The 3-axis Cartesian coordinate robot 352 includes three motors 354, 355 and 356. The first motor 354 provides a driving force in an X-axis direction, the second motor 355 provides a driving force in a Y-axis direction, and the third motor 356 provides a driving force in a Z-axis direction. Lead screws (not shown) accommodated in the 3-axis Cartesian coordinate robot 352 are connected to rotating shafts of the first to third motors 354, 355 and 356. The 3-axis Cartesian coordinate robot 352 is driven by the rotation of the lead screws. First to third encoders 357, 358 and 359 are respectively connected to first sides of the first to third motors 354, 355 and 356 so as to detect the rotational angle of the rotating shafts. That is, the 3-axis Cartesian coordinate robot 352 moves the position of the inlet nozzle 314 based on predetermined coordinates.

The 3-axis Cartesian coordinate robot 352 firstly matches the central axis of an outlet nozzle selected from the plural outlet nozzles 304 with the central axis of the inlet nozzle 314 based on the X-axis and Y-axis coordinates, and then, connects the selected outlet nozzle 304 to the inlet nozzle 314 by moving the outlet nozzle 304 along the Z-axis coordinate, while the inlet nozzle remains in a stationary position.

The apparatus for sampling deionized water and gases by using the fluid sampling apparatus according to the third embodiment of the present invention is similar to that of the second embodiment, so the detailed description thereof will be omitted.

Figure 16:
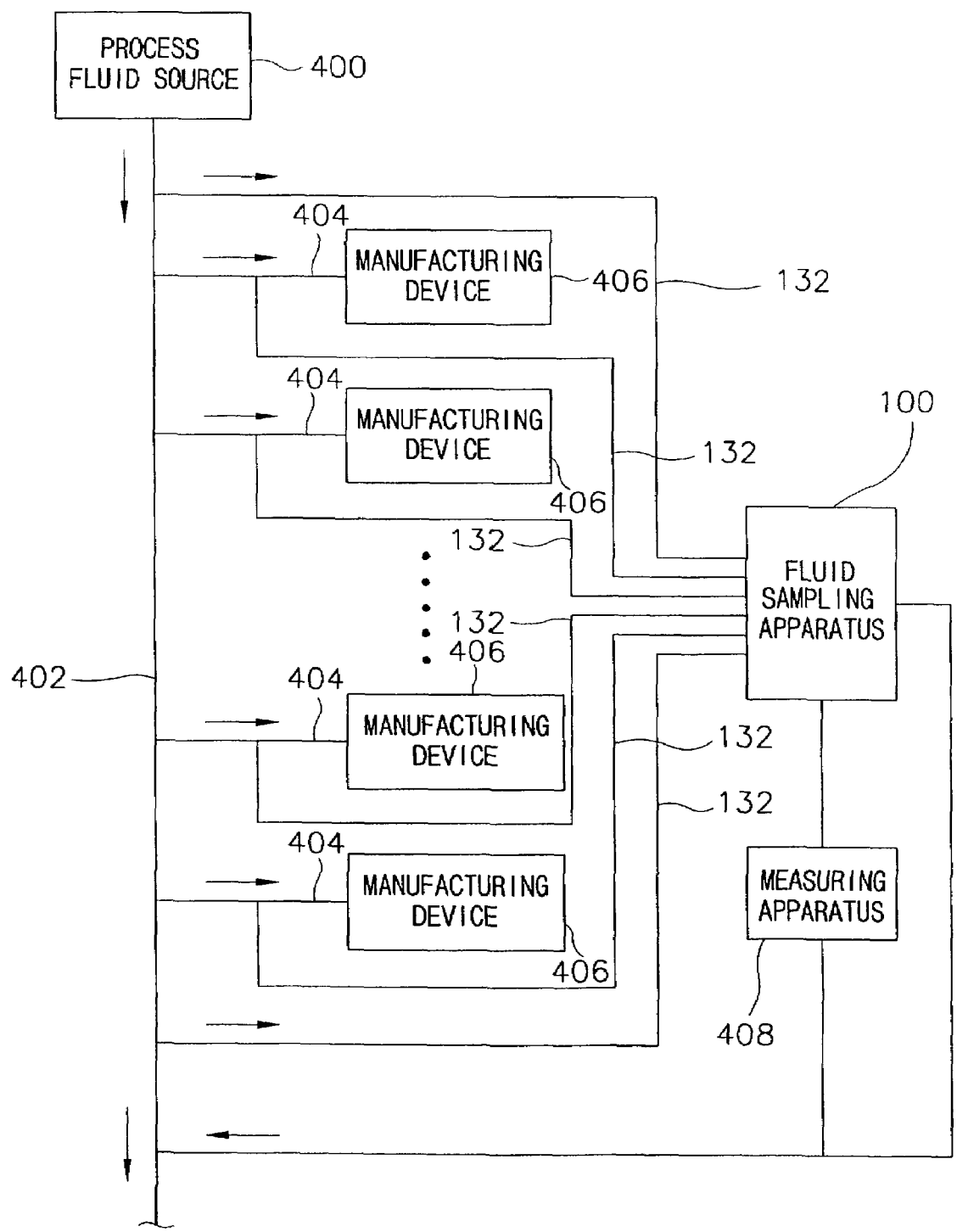
FIG. 16 is a block diagram illustrating the operation of process fluid supplying lines connected to the fluid sampling apparatus shown in FIG. 1.

FIG. 16 is a block view for illustrating the flow of fluids in the process fluid supplying lines connected to the fluid sampling apparatus shown in FIG. 1.

Referring to FIG. 16, the process fluid supplying lines are widely divided into a main line 402 connected to a process fluid source 400 and a plurality of sub-lines 404. The sub-lines 404 branch from the main line 402 and are connected to semiconductor manufacturing devices 406. The second sampling lines 132 connected to the fluid sampling apparatus 100 are connected to both main line 402 and sub-lines 404. That is, the second sampling lines 132 are connected to both starting point locations and ending point locations of the main line 402 connected to the process fluid source 400 and are connected to sub-lines 404 branching from the main line 402. Accordingly, it is possible to measure the contamination of the process fluids sampled from a plurality of measurement points using a single measuring apparatus 408.

FIG. 17 is a block diagram that illustrates the operation of the fluid analyzer including the fluid sampling apparatus shown in FIG. 1 and the measuring apparatus.

Referring to FIG. 17, the fluid analyzer includes the fluid sampling apparatus 100 for selectively supplying the process fluids from the second sampling lines 132 to the measuring apparatus. The process fluids include deionized water. Deionized water selected from the fluid sampling apparatus 100 is supplied to various measuring apparatus. The measuring apparatus include a particle counter 420, a dissolved oxygen measuring apparatus 422, a carbon content measuring apparatus 424, and a resistivity measuring apparatus 426. A flow rate adjusting section 428 for adjusting the flow rate of the process fluids to be adapted for each measuring apparatus is installed in the third sampling line 134, which connects each measuring apparatus to the fluid sampling apparatus 100. Deionized water passing through each measuring apparatus is discharged through the drain line 166.

Each measuring apparatus is connected to a data management section 440 so as to send measuring data to the data management section 440. The data management section 440 stores, compares and analyzes the measuring data. In addition, the data management section 440 manages the history of the measuring data with respect to each measuring point, and sends/receives the data to/from other fluid analyzer.

A display section 442 is connected to the data management section 440 to display the measuring result in a real time. The display section 442 also displays the stored measuring data and compared and analyzed data.

The fluid sampling apparatus 100 sequentially or selectively supplies the process fluids sampled from each measurement point to each measuring apparatus. In addition, the measuring result obtained by the measuring apparatuses is managed in the data management section 440. In one exemplary embodiment, one minute is needed for measuring the contamination level of the process fluids sampled from one measurement point. According to the preferred embodiment of the present invention, the number of the outlet nozzles is twenty-four, so twenty-four minutes are needed for measuring the contamination level of the process fluids supplied from each outlet nozzle. The above number of the outlet nozzles is determined by considering the length of a sampling line and the manufacturing process of the semiconductor device. However, the present invention in no way limits the number of the outlet nozzles or the sampling line lengths.

In this manner, the contamination level of the process fluids supplied from outlet nozzles can be continuously and repeatedly measured. Further, it is possible to continuously measure the process fluids supplied from a specific measurement point in real time.

In the case of gases including air, nitrogen, oxygen or argon, the number of particles is a primary reference point.

Though the present invention is described with reference to sampling of, and measurement of, deionized water, air, nitrogen, oxygen and argon, other process fluids with various measuring apparatuses can be adopted for the present invention.

As described above, according to the present invention, the process fluids supplied from the fluid lines, which supply the process fluids to semiconductor manufacturing devices, are selectively sampled by the fluid sampling apparatus and the sampled process fluids are supplied to the measuring apparatus. Accordingly, it is possible to measure the contamination level of the process fluids sampled from plural measurement points by using a single measuring apparatus. In addition, the data management section compares, analyzes, and stores plural measuring data and displays the measuring data in a real time through the display section, so the cleanliness of the process fluid is effectively managed.

Therefore, it is possible to effectively manage each sampling point and to prevent process faults are caused by the contamination of the process fluids. In addition, it is possible to rapidly correct the process fault by storing and managing the measuring data with respect to each sampling point.

Furthermore, by measuring the contamination level of the process fluids sampled from plural measurement points by using a single fluid analyzer, the cost in equipment investment and repair work can be lowered. In the present example, when the process fluids are sampled from twenty-four points, the equipment investment cost saved is more than 80%. When considering the cost of repair work and the expense of equipment, the cost-saving effect is even more greatly expanded.

In addition, since the cleanliness of the process fluids is particularly managed at plural measurement points, the reliability and productivity of the semiconductor devices can be improved.

While the present invention has been described in detail with reference to the preferred embodiments thereof, it should be understood to those skilled in the art that various changes, substitutions and alterations can be made hereto without departing from the scope of the invention as defined by the appended claims.

What is claimed is:

1. A fluid sampling apparatus comprising:
   a first nozzle assembly including a plurality of outlet nozzles, each having a first end that is fixed to one of a plurality of fluid lines, the outlet nozzles each supplying a flow of fluid from the corresponding fluid lines, wherein the first nozzle assembly further includes a first plate having a disc shape, the first plate including a plurality of first fluid passages passing through the first plate and formed along a periphery of the first plate, and wherein the outlet nozzles are connected to first sides of the first fluid passages;
   a second nozzle assembly installed in opposition to the first nozzle assembly and including an inlet nozzle that receives the flow of fluid from a selected one of the plurality of outlet nozzles, wherein the second nozzle assembly further includes a second plate having a disc shape, and wherein the inlet nozzle is connected to a first side of the second plate;
   a driving system that selects one of the outlet nozzles from the plurality of outlet nozzles, wherein in a first position, the driving system connects a second end of the selected one of the outlet nozzles with the inlet nozzle, and wherein in a second position, the driving system separates the second end of the selected one of the outlet nozzles from the inlet nozzle, wherein the driving system includes a rotating shaft connected to a central portion of the second plate, a motor connected to the rotating shaft for aligning the selected outlet nozzle with the inlet nozzle, and a pneumatic cylinder connected to the first plate for connecting and separating the selected outlet nozzle to and from the inlet nozzle, and
   a second fluid passage connected to the inlet nozzle passing through a central portion of the second plate to a center axis of the rotating shaft, wherein the second nozzle assembly further includes a plurality of auxiliary inlet nozzles connected to the first side of the second plate corresponding to the plurality of outlet nozzles other than the selected outlet nozzle, and a plurality of third fluid passages formed through the second plate along a periphery of the second plate, wherein the auxiliary inlet nozzles are connected to the third fluid passages, respectively.

2. The fluid sampling apparatus as claimed in claim 1, wherein the third fluid passages are each formed having a smaller cross-sectional area than a cross-sectional area of the second fluid passage.

3. The fluid sampling apparatus as claimed in claim 1, wherein the outlet nozzles and the inlet nozzle are comprised of polytetrafluoroethylene, and wherein the first and second plates are comprised of polytetrafluoroethylene or stainless steel.

4. The fluid sampling apparatus as claimed in claim 1, wherein first ends of the plurality of outlet nozzles are formed in a convex conical shape, and wherein a first end of the inlet nozzle is formed in a concave conical shape.

5. The fluid sampling apparatus as claimed in claim 1, further comprising a controller, in communication with the driving system so as to align the selected outlet nozzle with the inlet nozzle, the controller further controlling an operation of the driving system so as to reciprocate the second nozzle assembly for connecting and separating the selected nozzle to and from the inlet nozzle.

6. The fluid sampling apparatus as claimed in claim 1 further comprising a fluid supply connected by the fluid lines to the plurality of outlet nozzles, that supplies dionized water to the plurality of outlet nozzles for sampling.

7. The fluid sampling apparatus as claimed in claim 6, further comprising a container having the first and second nozzle assemblies therein and containing deionized water that is continuously supplied from the outlet nozzles, a drain line connected to a side portion of the container for draining the deionized water from the container, a water level detecting sensor installed in the container for detecting a level of deionized water, and a valve installed in the drain line for adjusting a draining rate of the deionized water based on a signal from the water level detecting sensor, wherein the first and second nozzle assemblies are immersed in the deionized water contained by the container.

8. The fluid sampling apparatus as claimed in claim 7, further comprising a plurality of first sampling lines connected to the outlet nozzles, a plurality of second sampling lines connected to the fluid lines, and a plurality of connectors installed at one side of the container for connecting the first sampling lines to the second sampling lines.

9. The fluid sampling apparatus as claimed in claim 1 further comprising a fluid supply connected by the fluid lines to the plurality of outlet nozzles, that supplies a fluid selected from the group consisting of air, nitrogen, oxygen, and argon to the plurality of outlet nozzles for sampling.

10. The fluid sampling apparatus as claimed in claim 9, further comprising an enclosed container containing the first and second nozzle assemblies therein, a drain line connected to the enclosed container for draining the fluid continuously supplied from the outlet nozzles into the enclosed container, a pressure sensor installed in the enclosed container for sensing an internal pressure in the enclosed container, and a valve installed in the drain line for adjusting a draining amount of the fluid based on a signal from the pressure sensor.

11. The fluid sampling apparatus as claimed in claim 9, further comprising an enclosed container having the first and second nozzle assemblies therein, a drain line connected to the enclosed container for draining the fluid continuously supplied from the outlet nozzles into the enclosed container, and a pressure control valve installed in the drain line for adjusting a draining amount of the fluid based on a change of an internal pressure in the enclosed container.

12. The fluid sampling apparatus as claimed in claim 1, wherein, when the driving system is in the second position, a distance between the outlet nozzle and the inlet nozzle is about 5 to 10 mm.

13. A fluid analyzer comprising:
a fluid sampling unit including a first nozzle assembly having a plurality of outlet nozzles connected to fluid lines for supplying a flow of fluid from the fluid lines, a second nozzle assembly installed in opposition to the first nozzle assembly and having an inlet nozzle that receives the fluid from a selected one of the outlet nozzles, and a driving system that selects the selected one of the outlet nozzles and that connects and separates the selected outlet nozzle to and from the inlet nozzle;
a measuring device connected to the inlet nozzle that measures a contamination level of the fluid supplied through the selected outlet nozzle and the inlet nozzle, wherein the measuring device includes a particle counter for measuring a number of particles contained in the fluid; and
a data management unit connected to the measuring device to store and manage data measured by the measuring device.

14. The fluid analyzer as claimed in claim 13, wherein the measuring device further includes a dissolved oxygen measuring apparatus, a carbon content measuring apparatus, and a resistivity measuring apparatus.

15. The fluid analyzer as claimed in claim 13, further comprising a flow rate adjusting section, installed at a line connecting the inlet nozzle to the measuring device so as to adjust a flow rate of the fluid supplied into the measuring device.

16. The fluid analyzer as claimed in claim 13, further comprising a display unit connected to the data management unit for displaying the data stored and measured by the measuring device in real time and for displaying the data stored in the data management unit.

17. A fluid sampling apparatus comprising:
a first nozzle assembly including a plurality of outlet nozzles, each having a first end that is fixed to one of a plurality of fluid lines, the outlet nozzles each supplying a flow of fluid from the corresponding fluid lines;
a second nozzle assembly installed in opposition to the first nozzle assembly and including an inlet nozzle that receives the flow of fluid from a selected one of the plurality of outlet nozzles; and
a driving system that selects one of the outlet nozzles from the plurality of outlet nozzles, wherein in a first position, the driving system connects a second end of the selected one of the outlet nozzles with the inlet nozzle, and wherein in a second position, the driving system separates the second end of the selected one of the outlet nozzles from the inlet nozzle, the fluid sampling apparatus further comprising a fluid supply connected by the fluid lines to the plurality of outlet nozzles, that supplies deionized water to the plurality of outlet nozzles, a container having the first and second nozzle assemblies therein and containing the deionized water that is continuously supplied from the outlet nozzles, a drain line connected to a side portion of the container for draining the deionized water from the container, a water level detecting sensor installed in the container for detecting a level of deionized water, and a valve installed in the drain line for adjusting a draining rate of the deionized water based on a signal from the water level detecting sensor, wherein the first and second nozzle assemblies are immersed in the deionized water contained by the container.

18. A fluid sampling apparatus comprising:
a first nozzle assembly including a plurality of outlet nozzles, each having a first end that is fixed to one of a plurality of fluid lines, the outlet nozzles each supplying a flow of fluid from the corresponding fluid lines;
a second nozzle assembly installed in opposition to the first nozzle assembly and including an inlet nozzle that receives the flow of fluid from a selected one of the plurality of outlet nozzles; and
a driving system that selects one of the outlet nozzles from the plurality of outlet nozzles, wherein in a first position, the driving system connects a second end of the selected one of the outlet nozzles with the inlet nozzle, and wherein in a second position, the driving system separates the second end of the selected one of the outlet nozzles from the inlet nozzle, the fluid sampling apparatus further comprising a fluid supply connected by the fluid lines to the plurality of outlet nozzles, that supplies a fluid selected from the group consisting of air, nitrogen, oxygen, and argon to the plurality of outlet nozzles, the fluid sampling apparatus further comprising an enclosed container containing the first and second nozzle assemblies therein, a drain line connected to the enclosed container for draining the fluid continuously supplied from the outlet nozzles into the enclosed container, a pressure sensor installed in the enclosed container for sensing an internal pressure in the enclosed container, and a valve installed in the drain line for adjusting a draining amount of the fluid based on a signal from the pressure sensor.

19. A fluid sampling apparatus comprising:
a first nozzle assembly including a plurality of outlet nozzles, each having a first end that is fixed to one of a plurality of fluid lines, the outlet nozzles each supplying a flow of fluid from the corresponding fluid lines;
a second nozzle assembly installed in opposition to the first nozzle assembly and including an inlet nozzle that receives the flow of fluid from a selected one of the plurality of outlet nozzles; and
a driving system that selects one of the outlet nozzles from the plurality of outlet nozzles, wherein in a first position, the driving system connects a second end of the selected one of the outlet nozzles with the inlet nozzle, and wherein in a second position, the driving system separates the second end of the selected one of the outlet nozzles from the inlet nozzle, the fluid sampling apparatus further comprising a fluid supply connected by the fluid lines to the plurality of outlet nozzles, that supplies a fluid selected from the group consisting of air, nitrogen, oxygen, and argon to the plurality of outlet nozzles, the fluid sampling apparatus further comprising an enclosed container having the first and second nozzle assemblies therein, a drain line connected to the enclosed container for draining the fluid continuously supplied from the outlet nozzles into the enclosed container, and a pressure control valve installed in the drain line for adjusting a draining amount of the fluid based on a change of an internal pressure in the enclosed container.

20. A fluid sampling apparatus comprising:
a first nozzle assembly including a plurality of outlet nozzles connected to fluid lines for supplying a fluid from the fluid lines, wherein the first nozzle assembly further includes a first plate having a disc shape, the first plate including a plurality of first fluid passages passing through the first plate and formed along a periphery of the first plate, and wherein the outlet nozzles are connected to first sides of the first fluid passages;
a second nozzle assembly installed in opposition to the first nozzle assembly and including an inlet nozzle for receiving the fluid from a selected one of the plurality of outlet nozzles, wherein the second nozzle assembly further includes a second plate having a disc shape, and wherein the inlet nozzle is connected to a first side of the second plate;
a driving system for selecting one of the outlet nozzles from the plurality of outlet nozzles and for connecting the selected one of the outlet nozzles with the inlet nozzle and for separating the selected one of the outlet nozzles from the inlet nozzle, wherein the driving system includes a rotating shaft connected to a central portion of the second plate, a motor connected to the rotating shaft for aligning the selected outlet nozzle with the inlet nozzle, and a pneumatic cylinder connected to the first plate for connecting and separating the selected outlet nozzle to and from the inlet nozzle; and
a second fluid passage connected to the inlet nozzle passing through a central portion of the second plate to a center axis of the rotating shaft, wherein the second nozzle assembly further includes a plurality of auxiliary inlet nozzles connected to the first side of the second plate corresponding to the plurality of outlet nozzles other than the selected outlet nozzle, and a plurality of third fluid passages formed through the second plate along a periphery of the second plate, wherein the auxiliary inlet nozzles are connected to the third fluid passages, respectively.

21. A fluid sampling apparatus comprising:
a first nozzle assembly including a plurality of outlet nozzles connected to fluid lines for supplying a fluid from the fluid lines;
a second nozzle assembly installed in opposition to the first nozzle assembly and including an inlet nozzle for receiving the fluid from a selected one of the plurality of outlet nozzles; and
a driving system for selecting one of the outlet nozzles from the plurality of outlet nozzles and for connecting the selected one of the outlet nozzles with the inlet nozzle and for separating the selected one of the outlet nozzles from the inlet nozzle, the fluid sampling apparatus further comprising a fluid supply connected by the fluid lines to the plurality of outlet nozzles, that supplies dionized water to the plurality of outlet nozzles, a container having the first and second nozzle assemblies therein and containing the deionized water that is continuously supplied from the outlet nozzles, a drain line connected to a side portion of the container for draining the deionized water from the container, a water level detecting sensor installed in the container for detecting a level of deionized water, and a valve installed in the drain line for adjusting a draining rate of the deionized water based on a signal from the water level detecting sensor, wherein the first and second nozzle assemblies are immersed in the deionized water contained by the container.

22. A fluid sampling apparatus comprising:
a first nozzle assembly including a plurality of outlet nozzles connected to fluid lines for supplying a fluid from the fluid lines;
a second nozzle assembly installed in opposition to the first nozzle assembly and including an inlet nozzle for receiving the fluid from a selected one of the plurality of outlet nozzles; and
a driving system for selecting one of the outlet nozzles from the plurality of outlet nozzles and for connecting the selected one of the outlet nozzles with the inlet nozzle and for separating the selected one of the outlet nozzles from the inlet nozzle, the fluid sampling apparatus further comprising a fluid supply connected by the fluid lines to the plurality of outlet nozzles, that supplies a fluid selected from the group consisting of air, nitrogen, oxygen, and argon to the plurality of outlet nozzles, the fluid sampling apparatus further comprising an enclosed container containing the first and second nozzle assemblies therein, a drain line connected to the enclosed container for draining the fluid continuously supplied from the outlet nozzles into the enclosed container, a pressure sensor installed in the enclosed container for sensing an internal pressure in the enclosed container, and a valve installed in the drain line for adjusting a draining amount of the fluid based on a signal from the pressure sensor.

23. A fluid sampling apparatus comprising:
a first nozzle assembly including a plurality of outlet nozzles connected to fluid lines for supplying a fluid from the fluid lines;
a second nozzle assembly installed in opposition to the first nozzle assembly and including an inlet nozzle for receiving the fluid from a selected one of the plurality of outlet nozzles; and
a driving system for selecting one of the outlet nozzles from the plurality of outlet nozzles and for connecting the selected one of the outlet nozzles with the inlet nozzle and for separating the selected one of the outlet nozzles from the inlet nozzle, the fluid sampling apparatus further comprising a fluid supply connected by the fluid lines to the plurality of outlet nozzles, that supplies a fluid selected from the group consisting of air, nitrogen, oxygen, and argon to the plurality of outlet nozzles, the fluid sampling apparatus further comprising an enclosed container having the first and second nozzle assemblies therein, a drain line connected to the enclosed container for draining the fluid continuously supplied from the outlet nozzles into the enclosed container, and a pressure control valve installed in the drain line for adjusting a draining amount of the fluid based on a change of an internal pressure in the enclosed container.

24. A fluid analyzer comprising:
a fluid sampling unit including a first nozzle assembly having a plurality of outlet nozzles connected to fluid lines for supplying a fluid from the fluid lines, a second nozzle assembly installed in opposition to the first nozzle assembly and having an inlet nozzle for receiving the fluid from a selected one of the outlet nozzles, and a driving system for selecting the selected one of the outlet nozzles and for connecting and separating the selected outlet nozzle to and from the inlet nozzle;
a measuring device connected to the inlet nozzle for measuring a contamination level of the fluid supplied through the selected outlet nozzle and the inlet nozzle, wherein the measuring device includes a particle counter for measuring a number of particles contained in the fluid; and
a data management unit connected to the measuring device to store and manage data measured by the measuring device.

* * * * *